United States Patent
Wang et al.

(10) Patent No.: US 7,060,467 B2
(45) Date of Patent: Jun. 13, 2006

(54) RECOMBINANT PROTEINS CONTAINING REPEATING UNITS

(75) Inventors: Qi Wang, Valley Park, MO (US); Zhonghon Guan, Chesterfield, MO (US); Brendan O. Baggot, Granite City, IL (US); Kristen Hadfield, Davis, CA (US); Jianmin Zhao, St. Louis, MO (US); Janice Edwards, University City, MO (US)

(73) Assignee: Monsanto Technology LLC, St. Louis, MO (US)

( * ) Notice: Subject to any disclaimer, the term of this patent is extended or adjusted under 35 U.S.C. 154(b) by 223 days.

(21) Appl. No.: 09/804,733

(22) Filed: Mar. 13, 2001

(65) Prior Publication Data

US 2002/0059656 A1 May 16, 2002

Related U.S. Application Data

(60) Provisional application No. 60/188,990, filed on Mar. 13, 2000.

(51) Int. Cl.
- C12N 15/64 (2006.01)
- C12N 15/00 (2006.01)
- C12N 15/09 (2006.01)
- C12N 15/63 (2006.01)
- C12P 19/34 (2006.01)

(52) U.S. Cl. ............... 435/91.4; 435/91.1; 435/320.1; 435/235.1; 435/69.1; 435/455; 435/471; 435/325; 536/23.1; 536/24.1; 536/23.4

(58) Field of Classification Search ............... 435/91.1, 435/91.4, 320.1, 235.1, 471, 325, 252.3, 435/440, 91.5, 419, 468, 69.1, 455; 536/23.1, 536/24.1, 23.4
See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 4,703,004 A | 10/1987 | Hopp et al. | |
| 4,782,137 A | 11/1988 | Hopp et al. | |
| 4,800,159 A | 1/1989 | Mullis et al. | |
| 4,845,341 A | 7/1989 | Rae | |
| 4,873,191 A | 10/1989 | Wagner et al. | |
| 4,973,679 A | 11/1990 | Caruthers et al. | |
| 5,023,171 A | 6/1991 | Ho et al. ................. | 435/6 |
| 5,071,955 A | 12/1991 | Mimura et al. | |
| 5,106,739 A | 4/1992 | Comai et al. | |
| 5,149,657 A | 9/1992 | Maugh et al. | |

(Continued)

FOREIGN PATENT DOCUMENTS

EP 347931 A2 12/1989

(Continued)

OTHER PUBLICATIONS

Fujita et al., LKPNM: A Prodrug-type ACE-inhibitory Peptide Derived from Fish Protein, Immunopharmacology 44 (1999) 123-127.

(Continued)

*Primary Examiner*—James Ketter
*Assistant Examiner*—Konstantina Katcheves
(74) *Attorney, Agent, or Firm*—Fulbright & Jaworski L.L.P.

(57) ABSTRACT

Methods for the production of recombinant proteins containing repeating units are disclosed. Also disclosed are methods for the production of degenerate polynucleotides encoding said recombinant proteins. In addition, polypeptides and polynucleotides produced by the methods of current invention are also disclosed.

20 Claims, 6 Drawing Sheets

$5'-S_n\ S_n\ S_n\ S_{10}$
$5'-S_n\ S_n\ S_n\ S_n$
$5'-S_n\ S_n\ S_n\ S_n$
$5'-S_{30}\ S_n\ S_n\ S_n$ $5'-C_{25}\ C_n\ C_n\ C_{10}$
$5'-C_n\ C_n\ C_n\ C_{25}$
$5'-C_n\ C_n\ C_n\ C_n$
$5'-C_{30}\ C_n\ C_n\ C_n$

ANNEAL $5'-S_{30}\ S_n\ S_n\ S_n$
$\quad\quad C_n\ C_n\ C_n\ C_{30}-5'$ $5'-S_n\ S_n\ S_n\ S_{10}$
$\quad\quad C_{10}\ C_n\ C_n\ C_{25}-5'$

EXTENSION $5'-S_n\ S_n\ S_n\ S_{10}\ S_n\ S_n\ S_{25}$
$\quad C_n\ C_n\ C_n\ C_{10}\ C_n\ C_n\ C_{25}-5'$

DENATURE AND ANNEAL $5'-\ S_n\ S_n\ S_n\ S_{10}\ S_n\ S_n\ S_{25}$
$\quad\quad\quad\quad\quad C_{25}\ C_n\ C_n\ C_n-5'$

U.S. PATENT DOCUMENTS

| | | | |
|---|---|---|---|
| 5,238,932 A | 8/1993 | Flynn et al. | |
| 5,243,038 A | 9/1993 | Ferrari et al. | |
| 5,451,513 A | 9/1995 | Maliga et al. | |
| 5,576,198 A | 11/1996 | McBride et al. | |
| 5,594,115 A | 1/1997 | Sharma | |
| 5,608,152 A | 3/1997 | Kridl et al. | |
| 5,693,507 A | 12/1997 | Daniell et al. | |
| 5,753,475 A | 5/1998 | Houck | |
| 5,811,636 A | 9/1998 | Hanna et al. | |
| 5,935,824 A | 8/1999 | Sgarlato | |
| 6,018,030 A | 1/2000 | Ferrari et al. | |

FOREIGN PATENT DOCUMENTS

| | | | |
|---|---|---|---|
| EP | 0255378 B1 | 4/1994 | |
| EP | 0812911 A2 * | 12/1997 | ............... 435/91.4 |
| EP | 812911 A2 | 12/1997 | |
| EP | 838473 A1 | 4/1998 | |
| WO | WO 95/16783 | 6/1995 | |
| WO | WO 95/24492 | 9/1995 | |
| WO | WO 95/24493 | 9/1995 | |
| WO | WO 96/05296 A1 | 2/1996 | |
| WO | WO 98/10063 A1 | 3/1998 | |

OTHER PUBLICATIONS

Astawan et al., Effects of Angiotensin I-Converting Enzyme Inhibitory Substances Derived from Indonesian Dried-salted fish on Blood Pressure of Rats, *Bioscience, Biotech., and Biochem.*, Mar. 1995, pp. 425-429, vol. 59, No. 3, Japan Society for Bioscience, Biotechnology and Agrochemistry, Japan.

Beaucage et al., Deoxynucleoside Phosphoramidites-A New Class Of Key Intermediates For Deoxypolynucleotide Synthesis, *Tetra. Letters*, 1981, pp. 1859-1862, vol. 22, No. 20.

Clark et al., Mutations at the Transit Peptide-Mature Protein Junction Separate Two Cleavage Events during Chloroplast Import of the Chlorophyll a/b-binding Protein, *J. Biol. Chem.*, Oct. 1989, pp. 17544-17550, vol. 264, No. 29, Amer. Society for Biochemistry and Molecular Biology, Inc., USA.

Colman, Production of therapeutic proteins in the milk of transgenic livestock, *Mammary Development and Cancer*, 1998, pp. 141-147, vol. 63, The Biochemical Society, London, Great Britain.

Dalrymple et al., Genetically Modified Livestock for the Production of Human Proteins in Milk, *Biotechnology and Genetic Engineering Reviews*, Apr. 1998, pp. 33-49, vol. 15, Intercept Ltd., United Kingdom.

Della-Cioppa et al., Protein Trafficking in Plant Cells, *Plant Physiol.*, 1987, pp. 965-968, vol. 84.

Fisk et al., The introduction and expression of transgenes in plants, *Scientia Horticulture*, Aug. 1993, pp. 5-36, vol. 55, Nos. 1-2, Elsevier Science Publishers B.V.

Gasser et al., Genetically Engineering Plants for Crop Improvement. *Science*, Jun. 1989, pp. 1293-1299, vol. 244, Amer. Assoc. for the Advancement of Science, Washington, D.C., USA.

Lam et al., Tetramer of a 21-Base Pair Synthetic Element Confers Seed Expression and Transcriptional Enhancement in Response to Water Stress and Abscisic Acid, *J. Biol. Chem.*, Sep. 1991, pp. 17131-17135, vol. 266, No. 26, Amer. Society for Biochemistry & Molecular Biology, USA.

Messing, New M13 Vectors for Cloning, *Methods in Enzymology*, 1983, pp. 20-79, vol. 101, Academic Press, Inc.

Nawrath et al., *Proc. Natl. Acad. Sci.*, Dec. 1994, pp. 12760-12764, vol. 91, No. 26, National Academy of Sciences, Washington, D.C., USA.

Odell et al., Identification of DNA sequences required for activity of the cauliflower mosaic virus 35S promoter, *Nature*. Feb. 1985, pp. 810-812, vol. 313, No. 6005, Macmillan Journals, Ltd.

Padgette et al., Development, Identification, and Characterization of a Glyphosphate-Tolerant Soybean Line, *Crop Science*, 1995, pp. 1451-1461, vol. 35, No. 5, Crop Science Society of America, Inc., USA.

Perry et al., Transgenesis in chickens, *Transgenic Research*, May 1993, pp. 126-133, vol. 2, No. 3, Chapman & Hall, London.

Potrykus, Gene Transfer to Plants: Assessment of Published Approaches and Results, *Annual Rev. of Plant Phys. and Plant Molec. Biol.*, 1991, pp. 205-223, Annual Reviews, Inc., Palo Alto, CA, USA.

Richins et al., Sequence of figwort mosaic virus DNA (caulimovirus group), *Nucleic Acids Research*, 1987, pp. 8451-8466, vol. 15, No. 20, IRL Press.

Romer et al., Expression of the Genes Encoding the Early Carotenoid Biosynthetic Enzymes in *Capsium Annuum*, *Biochem. and Biophys. Research Communications*, Nov. 1993, pp. 1414-1421, vol. 196, No. 3, Academic Press, Inc.

Rudolph, Biopharmaceutical production in transgenic livestock, Sep. 1999, pp. 367-374, vol. 17, No. 9, Elsevier Science Ltd.

Sadler et al., Plasmids Containing Many Tandem Copies Of A Synthetic Lactose Operator, *Gene*, Jan. 1980, pp. 279-301, vol. 8, No. 3, Elsevier/North-Holland Biomedical Press.

Shah et al., Engineering Herbicide Tolerance in Transgenic Plants, *Science*, Jul. 1986, pp. 478-481, vol. 25, No. 233, American Association for the Advancement of Science, Washington, D.C., USA.

Staub et al., Accumulation of D1 polypeptide in tobacco plastids is regulated via the untranslated region of the pshA mRNA. *The EMBO Journal*, 1993, pp. 601-606. vol. 12, No. 2, Oxford University Press.

Suetsuna, Immunostimulating Peptides Derived from Sardine Muscle and Soybean Protein; Amino Acid Sequence, Synthesis and Biological Properties, *Clinical Report*, Dec. 1991, pp. 4773-4784, vol. 25.

Svab et al., Stable transformation of plastids in higher plants, *Proc. Natl. Acad. Sci.*, Nov. 1990, pp. 8526-8530, vol. 87, No. 21, Natl. Academy of Sciences, USA.

Svab et al., *Proc. Natl. Acad. Sci.*, 1993, pp. 913-917, vol. 90, No. 3, Natl. Academy of Sciences, USA.

Von Heijne et al., CHLPEP-A Database of Chloroplast Transit Peptides, *Plant Molec. Biology Reporter*, May 1991, pp. 104-126, vol. 9, No. 2.

Walden et al., Gene-transfer and plant-regeneration techniques, *Biotechnology*, Sep. 1995, pp. 324-331, vol. 13, No. 4, Elsevier Science Ltd.

White et al., Concatemer Chain Reaction: A Taq DNA Polymerase-Mediated Mechanism for Generating Long Tandemly Repetitive DNA Sequences. *Anal. Biochem.*, Dec. 1991, pp. 184-190, vol. 199, No. 2, Academic Press, Inc.

* cited by examiner

FIG. 1A $5'-S_n\ S_n\ S_n\ S_{10}$          $5'-C_{25}\ C_n\ C_n\ C_{10}$ $5'-S_n\ S_n\ S_n\ S_n$          $5'-C_n\ C_n\ C_n\ C_{25}$ $5'-S_n\ S_n\ S_n\ S_n$          $5'-C_n\ C_n\ C_n\ C_n$ $5'-S_{30}\ S_n\ S_n\ S_n$          $5'-C_{30}\ C_n\ C_n\ C_n$

ANNEAL $5'-S_{30}\ S_n\ S_n\ S_n$
$C_n\ C_n\ C_n\ C_{30}-5'$ $5'-S_n\ S_n\ S_n\ S_{10}$
$C_{10}\ C_n\ C_n\ C_{25}-5'$

EXTENSION $5'-S_n\ S_n\ S_n\ S_{10}\ S_n\ S_n\ S_{25}$
$C_n\ C_n\ C_n\ C_{10}\ C_n\ C_n\ C_{25}-5'$

DENATURE AND ANNEAL $5'-\ S_n\ S_n\ S_n\ S_{10}\ S_n\ S_n\ S_{25}$
$C_{25}\ C_n\ C_n\ C_n-5'$

FIG. 1B

```
CTNAARCCNAAYATGCTNAARCCNAAYATGCTNAARCCNAAYATG
GANTTYGGNTTRTACGANTTYGGNTTRTACGANTTYGGNTTRTAC
                                                                    3'
5'
CTNAARCCNAAYATGCTNAARCCNAAYATGCTNAARCCNAAYATG
                           GANTTYGGNTTRTACGANTTYGGNTTRTACGANTTYGGNTTRTAC
                                                                    3'                                                                                 5'
5'
CTNAARCCNAAYATGCTNAARCCNAAYATGCTNAARCCNAAYATG- - - - - - - - - - - - - - - - - - - - - - - -  >
<- - - - - - - - - - - - - - - - - - - - - - - -GANTTYGGNTTRTACGANTTYGGNTTRTACGANTTYGGNTTRTAC
                                                                                                                           5'
                                                                                                                                                        3'
5'
CTNAARCCNAAYATGCTNAARCCNAAYATGCTNAARCCNAAYATGCTNAARCCNAAYATGCTNAARCCNAAYATG
GANTTYGGNTTRTACGANTTYGGNTTRTACGANTTYGGNTTRTACGANTTYGGNTTRTACGANTTYGGNTTRTAC
3'                                                                                                                                                      5'

CTNAARCCNAAYATGCTNAARCCNAAYATG..//..CTNAARCCNAAYATGCTNAARCCNAAYATGCTNAARCCNAAYATG
                                                                    GANTTYGGNTTRTACGANTTYGGNTTRTACGANTTYGGNTT..//.. GANTTYGGNTTRTAC

CTNAARCCNAAYATGCTNAARCCNAAYATG..//..CTNAARCCNAAYATGCTNAARCCNAAYATGCTNAARCCNAAYATG- - - - - - - - - - - - - - - - - - - - - - - - - - - - - >
<- - - - - - - - - - - - - - - - - - -GANTTYGGNTTRTACGANTTYGGNTTRTACGANTTYGGNTT..//.. GANTTYGGNTTRTAC
```

FIG. 7

Clone 11 (SEQ ID NO: 9)
CCATTACAATCCGGATATAGTTCCTCCTTCAGCAAAAAACCCCTCAAGAC
CCGTTAAAGGCCCAAGGGGTTATGCTAGTTAATTGCTCAGCGGTGGCAGC
AGCCAAACTCAGCTTCCTTTCGGCTTTTGTAACAGCCGGATCTCAAGTGG
TGGTGGTGGTGGTGCTCGAGTGCGGCCGCCATATTTGGCTTGAGCATATT
CGGTTTCAGCATGTTGGGCTTGAGCATATTCGGCTTGAGCATGTTAGGCT
TTAGCATGTTGGGCTTAAGCATATTGGGTTTTAGCATGTTCGGCTTCAGC
ATGTTGGGCTTCAGCATGTTGGGCTYGAGCATATTCGGYTWTAGCAAGTT
AGGTTTTAGCATGTTCGGCTTCAGCATGTTTGGCTTCAGCATATTTGGCT
TGAGGAATTCGGATCCGATATCAGCCATGGCCTTGTCGTCGTCGTCGG Clone 7 (SEQ ID NO: 10)
CTTCCTTTCGGGCTTTGTTAGCAGCCGGATCTCAGTGGTGGTGGTGGTGG
TGCTCGAGTGCGGCCGCCATGTTGGGTTTGAGCATATTAGGTTTCAGCAT
GTTCGGTTTCAGCATGTTCGGTTTTAGCATGTTTGGCTTAAGCATATTGG
GCTTGAGCATATTGGGCTTCAGCATGTTAGGCTTGAGCATATTGGGCTTC
AGCATGTTGGGCTTAAGCATGTTGGGCTTGAGCATGTTCGGCTTGAGCAT
ATTTGGTTTGAGCATGTTTGGCTTCAGCATATTAGGCTTAAGCATGTTGG
GTTTGAGCATATTTGGTTTTAGCATATTAGGTTTAAGCATGTTCGGCTTG
AGCATGTTGGGTTTCAGGAATTCGGATCCGATATCAGCCATGGCCTTGTC
GTCGTCGTCGGTACCCAGATCTGGGCTGTCCATGTGCTGGCGTTCGAATT
TAGCAGCAGCGGTTTCTTTCATACCAGAACCGCGTGGCACCAGACCAGAA
GAATGATGATGATGATGGTGCATATGTATATCTCCTTCTTAAAGTTAAAC
AAAATTATTTCTAGAGGGGAATTGTTATTCGC Clone 6 (SEQ ID NO: 11)
GCCCCAAGGGGTTATGCTAGTTATTGCTCAGCGGTGGCAGCAGCCAACTC
AGCTTCCTTTCGGGCTTTGTTAGCAGCCGGATCTCAGTGGTGGTGGTGGT
GGTGCTCGAGTGCGGCCGCCATATTTGGTTTGAGCATGTTCGGTTTAAGC
ATGTTCGGCTTGAGCATATTCGGCTTGAGCATGTTGGGTTTGAGCATATT
CGGCTTTAGGAATTCGGATCCGATATCAGCCATGGCCTTGTCGTCGTCGT
CGGTACCCAGATCTGGGCTGTCCATGTGCTGGCGTTCGAATTTAGCAGCA
GCGGTTTCTTTCATACCAGAACCGCGTGGCACCAGACCAGAAGAATGATG
ATGATGATGGTGCATATGTATATCTCCTTCTTAAAGTTAAACAAAATTAT
TTCTAGAGGGGAATTGTTATC Clone 2 (SEQ ID NO: 12)
GGTGGTGGTGGTGGTGCTCGAGTGCGGCCGCCATGTTCGGCTTCAGCATG
TTGGGTTTCAGCATGTTCGGCTTCAGCATATTCGGCTTGAGCATGTTTGG
CTTGAGCAAGTTAGGTTTCAGCATATTAKGTTTAAGCATATTAGGTTTAA
GCATATTAGGTTTAAGCATATTTGGCTTGAGCATGTTGGGCTTCAGCATG
TTCGGCTTCAGCATGTTCGGTTTGAGCATATTAGGCTTAAGCATGTTGGG
CTTCAGCATGTTCGGCTTCAGCATGTTAGGTTTWAGCATGTTTGGCTTGA
GCATGTTAGGCTTTAGGAATTCGGATCCAGAT

RECOMBINANT PROTEINS CONTAINING REPEATING UNITS

CROSS-REFERENCE TO RELATED APPLICATIONS

This application claims priority from U.S. Provisional Patent Application Ser. No. 60/188,990, filed Mar. 13, 2000, which is herein incorporated by reference in its entirety for all purposes.

FIELD OF THE INVENTION

This invention relates to the field of recombinant DNA technology and, more particularly, to methods for the production of recombinant polynucleotide sequences and recombinant proteins containing repeating sequences. The invention provides methods for the production of polynucleotides and/or proteins containing tandem repeats of short sequences in which complementary polynucleotides anneal and act as primers allowing extension of their 3' ends to produce long sequences of tandem repeats.

BACKGROUND

One of the major advances in molecular biology has been the ability to produce recombinant proteins, especially proteins which have therapeutic value. Recombinant polynucleotides encoding the proteins of interest can be introduced by way of expression vectors into any number of host cells which will then produce the desired protein. This technique is especially useful for the production of short peptides, particularly those which do not require extensive post-translational modification for biological activity.

Current manufacturing procedures allow for several methods for the manufacture of proteins. One such method includes the use of peptide synthesizers designed for research purposes. Production of small peptides of high value has been accomplished by peptide synthesizers in the past. Advances in peptide synthesis in the last 30 years have allowed the synthesis of peptides of up to approximately 120 amino acids long. While the technical peptide length limit is approximately 100–120, the yield drops off with increasing length. This fundamental yield limitation leads to drastically increased cost for synthesizing long peptides or for synthesizing large quantities of small peptides. For this and other reasons, the industrial scale synthesis of peptides via peptide synthesizers, chemical synthesis, or manual synthesis is not feasible for long peptides and proteins.

A second method includes the production of peptides through microbial fermentation. A number of peptides have been synthesized in this fashion including human insulin in yeast. This method may or may not be suitable depending on the size of the protein and the post-translational modification required.

A third method is the use of transgenic plants. Transgenic plants can be used as factories to produce proteins on a tons per year scale. Transgenic plants do not require the large investment in infrastructure that is required with large scale production of proteins by fermentation and plants can be consumed directly, thus eliminating the need to purify the protein. In addition, facilities for the harvesting, storage and processing of plants are largely in place. Edible transgenic plants also provide a means by which peptides of nutritional or therapeutic value can be administered without further processing through the direct consumption of the plants, their seeds or fruits, or edible products made from the plants.

The development of the polymerase chain reaction (PCR) has greatly aided in the production of recombinant polynucleotides for host cell transformation. The basic PCR procedure, which is described in U.S. Pat. Nos. 4,683,202, 4,683,195 and 4,800,159, typically involves the treatment of a double-stranded polynucleotide template with a pair of oligonucleotide primers which flank the sequence of interest. Conditions are manipulated so that the primers bind to the complementary templates and extension of the 3' ends of each primer results in production of two new double stranded polynucleotides containing the sequence of interest. The newly produced polynucleotides are then denatured, usually by heating, and the process of primer annealing and extension repeated. By repeating the process many times, copies of the desired sequence can be produced in an exponential fashion. Using PCR, it is possible to rapidly produce large numbers of recombinant polynucleotides for host cell transformation. In addition, variations on the basic PCR technique allow for such things as the introduction of restriction enzyme cleavage sites, site directed and random mutations, and the production of chimeric proteins.

As part of the PCR reaction, the primers used become part of the newly synthesized molecule. In most cases, the presence of the primers does not create a problem since the value of the protein produced is not affected by the presence of the primers. In many cases, the presence of the primers is an advantage, because they allow the introduction of mutations, cleavage sites for the introduction of the sequence into a vector, or sites which can be used to link several sequences together to produce a longer sequence than can normally be produced using PCR alone.

One type of polynucleotide that can be produced by PCR is that which contains tandem repeats. Tandem repeats are especially useful in the production of short peptides. During expression of the protein encoded by the sequence, the presence of large numbers of small molecules can create an osmotic stress on the host cell. This osmotic stress can result in decreased translation or in extreme cases death of the host cell, thus limiting the amount of the protein produced in plants. The osmotic stress can be decreased, if instead of producing many small molecules, a lesser number of large protein molecules each containing multiple copies of the peptide are produced. These large protein molecules can then be processed to produce the smaller peptides.

Methods have been developed for the production of recombinant proteins containing repeating units. For example, Sadler et al. ((1980) *Gene* 8:279–300) discloses plasmids containing tandem repeats of a synthetic lactose operator constructed by combining Tinkered 40 base operator fragments. Gupta et al. ((1983) *Bio/Technology* 1:602–609) reports the construction of repeats of a palindromic dodecamer by annealing and ligation. Maugh et al. (U.S. Pat. No. 5,149,657) and Ferrari et al. (U.S. Pat. Nos. 5,243,038 and 6,018,030) teach the production polypeptides containing repeats of adhesive proteins by ligation of individual fragments. Although effective, production of nucleotide sequences containing tandem repeats by ligation is slow, labor intensive, and does not result in the rapid production of polynucleotides such as is possible with PCR.

White et al., ((1991) *Anal. Biochem.*, 199:184–190) disclose a method for the production of polynucleotides containing repeating units in which oligonucleotide and partially complimentary linker pairs are ligated together to form concatemers. These concatemers then serve as templates in a PCR reaction which may or may not contain supplemental primers. In a variation, the oligonucleotide and linker pairs are not ligated together to form concatemers, but are simply combined in the PCR reaction mixture, where their complementary portions anneal to for a double stranded complex with single stranded extensions at their 5' ends. White et al. teach the use of the products produced as hybridization probes, or targets in applications such as run-on transcription or analysis of repetitive DNA sequences. White et al. does not teach or suggest the use of the method for the production of polypeptides containing repeating units.

One limitation of many of the prior art methods is the presence of linkers within the polynucleotides produced. As with primers, the presence of linkers can serve useful functions, for example, providing a cleavage site for inserting the polynucleotide into an expression vector or encoding a cleavage site to allow isolation of the individual peptides after expression. The are some circumstances, however, where the elimination of linkers in repetitive polypeptides may be advantageous, for example, in small bioactive peptides where the presence of even a single additional amino acid can have a marked effect on biological function. In such instances, the presence of the linker or remnants of the linker following cleavage can have a detrimental effect on activity and requires that the linkers be cleaved from the peptide which then must be separated from the free linkers in order to obtain a purified product. The increased number of steps required can greatly add to the cost of production for peptides that are produced in large quantities. The present invention provides for the efficient assembly of repeating polynucleotides with or without intervening linkers or sequences.

An additional problem with polynucleotides containing tandem repeats is stability within a host cell. Gupta et al. ((1983) *Bio/Techniques,* 1:602–609), reported that a palindromic DNA containing a dodecamer was stable only when its size did not exceed 120 base pairs. The same authors noted, however, that stability could be achieve by insertion of a nonpalindromic sequence. Such a solution is not feasible, however, in the situation where the inclusion of additional sequences is undesirable. An alternative solution exploits the degeneracy in the genetic code. See e.g. U.S. Pat. Nos. 5,149,657 and 5,243,038. In this method, different codons are used resulting in sequences which encode the same amino acid sequence, but which contain different nucleotide sequences. In this way, the repetitiveness of the nucleotide sequence is decreased, resulting in greater stability. Until the present invention, however, degenerate sequences have not be used in conjunction with nucleotide chain extension reactions such as PCR. Instead, degenerate sequences were synthesized, ligated together and repeatedly inserted into vectors to produce sequences with large numbers of repeats. Previous methods to produce tandem repeats by chain extension, have utilized sequences of known composition. Supposedly this was done to insure proper annealing which is necessary for chain extension to take place. What is needed, therefore, is a method for the rapid production by chain extension of nucleotide sequences encoding repeating peptides wherein the nucleotide sequences utilized exploit the degeneracy of the genetic code. The present invention meets that need.

The present inventors have surprisingly discovered a novel method by which it is possible to rapidly produce nucleotide sequences with high, preferably maximum, degeneracy encoding repeating peptide units by chain extension. Unlike previous methods, the present invention does not require that the exact sequences of the oligonucleotides used in the chain extension reaction be known. Rather, oligonucleotides can be used that have been synthesized to result in the greatest possible variation in nucleotide sequence allowed by the genetic code. Thus, the present invention provides a novel method for the rapid, economical production of highly stable nucleotide sequences encoding large repeating protein molecules.

SUMMARY

Methods are provided for the rapid and efficient production of polynucleotide sequences encoding proteins containing tandem repeats. Also provided are methods for using such polynucleotides to produce recombinant proteins, especially bioactive peptides in a variety of host cells.

Accordingly, one aspect of the present invention is a method for the production of a polynucleotide encoding at least one tandem repeat of an amino acid sequence. The method involves providing a first pool of polynucleotides encoding at least one tandem repeat of an amino acid sequence wherein the polynucleotides are degenerate in accordance with the genetic code. A second pool of degenerate polynucleotides is also provided at least some members of which are complementary to the polynucleotides of the first pool. The polynucleotides are then combined under conditions whereby they will anneal. After the polynucleotides are annealed, the 3' end of each annealed pair is extended under conditions where the polynucleotides serve the functions of both template and primer. Following extension, the newly extended polynucleotides are denatured. The annealing, extension and denaturation steps are then repeated at least once.

Another aspect of the present invention provides a method for the production of a polynucleotide encoding at least one tandem repeat of an amino sequence in which there is an absence of intervening amino acids between the tandem repeats. The method involves providing a first pool of polynucleotides encoding at least one tandem repeat of an amino acid sequence where there are no intervening amino acids between the repeats and the polynucleotides are degenerate in accordance with the genetic code. A second pool of degenerate polynucleotides is also provided at least some members of which are complementary to the polynucleotides of the first pool. The polynucleotides are then combined under conditions whereby they will anneal. After the polynucleotides are annealed, the 3' ends of each annealed pair is extended under conditions where the polynucleotides serve the functions of both template and primer. Following extension, the newly extended polynucleotides are denatured. The annealing, extension and denaturation steps are then repeated at least once. In one embodiment, said tandem repeats are separated by no more than nine nucleotides.

Yet another aspect of the present invention is a method for the production of recombinant proteins containing repeated sequences. The method involves providing a first pool of polynucleotides encoding at least one tandem repeat of an amino acid sequence where the polynucleotides are degenerate in accordance with the genetic code. A second pool of degenerate polynucleotides is also provided some members of which are complementary to the first pool of polynucleotides. The polynucleotides are then combined under conditions whereby they will anneal. After the polynucleotides are annealed, the 3' ends of each pair of polynucleotides is extended under conditions where the polynucleotides serve the functions of both template and primer. Following extension, the newly extended polynucleotides are denatured. The annealing, extension and denaturation steps are then repeated at least once. After completion of the extension steps, if desired, one or more linker sequences may be added to either or both ends of the polynucleotides produced. The polynucleotides produced, with or without linkers, are then inserted into a suitable expression vector which is then introduced into a suitable host cell. The host cell is grown and subjected to conditions which will cause expression of the recombinant protein. Following expression, the recombinant protein is then isolated from the host cell itself or the medium in which the host cell is grown. In one embodiment, said tandem repeats are separated by no more than nine nucleotides.

Still another aspect of the present invention is a method for the production of recombinant proteins by the use of polynucleotides containing repeated sequences with no intervening amino acids between the repeats. The method involves providing a first polynucleotide encoding at least one tandem repeat of an amino acid sequence where there are no intervening amino acids between the repeats and the polynucleotides are degenerate in accordance with the genetic code. A second pool of degenerate polynucleotides is also provided at least some members of which are complementary to the first pool of polynucleotides. The polynucleotides are then combined under conditions whereby they will anneal. After the polynucleotides are annealed, the 3' ends of each annealed pair is extended under conditions where the polynucleotides serve the functions of both template and primer. Following extension, the newly extended polynucleotides are denatured. The annealing, extension and denaturation steps are then repeated at least once. After completion of the extension steps, if desired, one or more linker sequences may be added to either or both ends of the polynucleotide produced. The polynucleotides produced, with or without linkers, are then inserted into a suitable expression vector which is then introduced into a suitable host cell. The host cell is grown and subjected to conditions which will cause expression of the recombinant protein. Following expression, the recombinant protein is then isolated from the host cell itself or the medium in which the host cell is grown.

In yet another aspect, the host cell produced contains a second vector containing a nucleotide sequence encoding an enzyme that will cleave between the repeats to produce single peptide units. In another aspect, this second vector can contain an organelle or tissue specific promoter or a target sequence so the enzyme is targeted to a location different from the recombinant protein. This results in the enzyme being unable to cleave the recombinant protein until the two are mixed by, for example, cell lysis, homogenization or processing.

Still another aspect of the invention, provides a polynucleotide of the formula

Still another aspect of the invention, provides a polynucleotide of the formula $A_w [L_x S_n]_y B_z$ and its complement where, A is a nucleotide sequence containing at least one restriction enzyme site; L is a nucleotide sequence containing at least one chemical or enzymatic cleavage site; S is a degenerate nucleotide sequence encoding one of the amino acid sequences selected fiom the group consisting of LKPNM (SEQ ID NO:1), KPNM (SEQ ID NO:2). VVYP (SEQ NO:3), KPN, DKP, YKP EKP, DAP, EAP, HPP, VPP, LK, PN and NM such that S's with different values of n comprise different nucleotide sequences, but encode the same amino acid sequence; B is a nucleotide sequence containing at least one restriction enzyme site, where B may or may not be the same as A; w is 0 or 1; x is 0 or 1; n varies randomly with each S, and is a whole number fiom 1 to the maximum number of possible nucleotide sequences encoding the amino acid sequence of S; y is at least 2; and z is 0 or 1.

In another aspect of the invention, is provided a polynucleotide of the formula $A_w [L_x S_n T_m]_y B_z$ and its complement where, A is a nucleotide sequence containing at least one restriction enzyme site; L is a nucleotide sequence containing at least one chemical or enzymatic cleavage site; S is a degenerate nucleotide sequence encoding one of the amino acid sequences selected from the group consisting of LKPNM (SEQ ID NO:1), KPNM (SEQ ID NO:2). VVYP (SEQ ID NO:3), KPN, DKP, YKP EKP, DAP, EAP, HPP, VPP, LK, PN and NM such that S's with different values of n comprise different nucleotide sequences, but encode the same amino acid sequence; T is a degenerate nucleotide sequence encoding one of the amino acid sequences selected from the group consisting of LKPNM (SEQ ID NO:1), KPNM (SEQ ID NO:2). VVYP (SEQ ID NO:3), KPN, DKP,YKP EKP, DAP, EAP, HPP, VPP, LK, PN and NM such that the sequence of T encodes an amino acid sequence different from S, and T's with different values of m comprise different nucleotide sequences, but encode the same amino acid sequence; B is a nucleotide sequence containing at least one restriction enzyme site, where B may or may not be the same as A; w is 0 or 1; x is 0 or 1; n varies randomly with each S, and is a whole number from 1 to the maximum number of possible nucleotide sequences encoding the amino acid sequence of S; m varies randomly with each T, and is a whole number from 1 to the maximum number of possible nucleotide sequences encoding the amino acid sequence of T; y is at least 2; and z is 0 or 1.

BRIEF DESCRIPTION OF THE DRAWINGS

These and other features, aspects, and advantages of the present invention will become better understood with regard to the following description, appended claims and accompanying figures where:

FIG. 1A shows a representation of the method by which polynucleotides containing repeated sequences are produced. Although not required to practice every embodiment of the invention, in this representation, there are no intervening nucleotides between the repeats. In the Figure, S is a polynucleotide sequence encoding a peptide and C is a complementary sequence. The subscript n is a number between 1 and the maximum number of possible sequences encoding the same peptide, such that two S's with different values of n would differ in their nucleotide sequence while encoding the same peptide. Within each group of four S's or C's, the value of n varies randomly.

FIG. 1B shows the same information as FIG. 1A, except that S and C have been replaced with the nucleotide sequences, represented by SEQ ID NO:30 and SEQ ID NO:31 respetively, used in the Examples. Although not required to practice every embodiment of the invention, in this representation there are no intervening nucleotides between the repeats.

FIG. 7 shows the sequences of the polynucleotides produced by the method of the present invention from clones 2, 6, 7 and 11, respectively. All sequences are shown 5' to 3'.

DEFINITIONS

Figure 2:
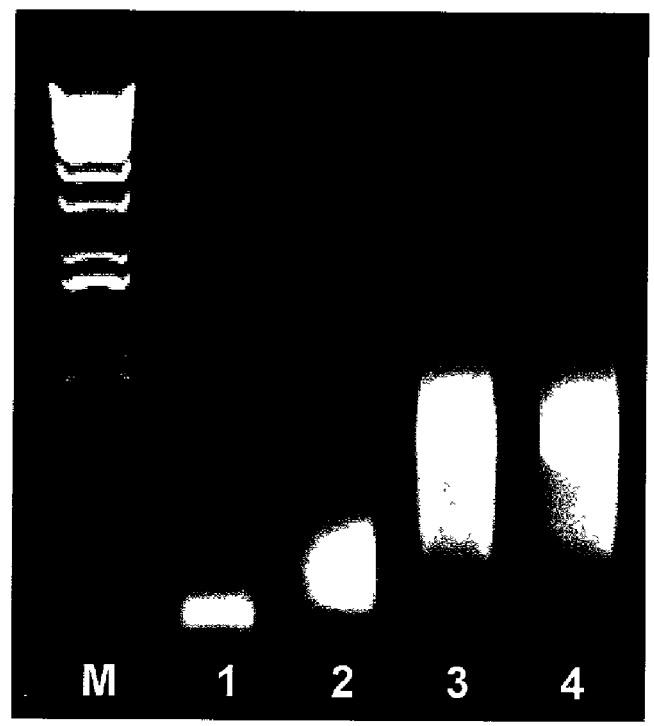
FIG. 2 shows an agarose gel of polynucleotides with repeating units made by the present method. Lane M=size makers, Lane 1=products after 0 cylces (starting polynucleotides), Lane 2=products after 30 cycles, and Lane 3=products after 60 cycles.

As use herein, the term "tandem repeat(s)" means either multiple copies of a nucleotide sequence which encodes the same amino acid sequence within a single polynucleotide or repeating amino acid sequences within a single peptide or protein. Tandem repeats may or may not contain intervening nucleotide or amino acid sequences.

As used herein, a "recombinant" polynucleotide or polypeptide is defined either by its method of production or its structure. In reference to its method of production, e.g., a product made by a process, the process involved uses of recombinant nucleic acid techniques. In reference to structure, recombinant polynucleotides or polypeptides contain sequences from different sources. In particular, it encompasses polynucleotides and polypeptides made by generating a sequence comprising two or more fragments which are not naturally contiguous or operably linked to each other. Thus, for example, products made by transforming cells with any unnaturally occurring vector are encompassed.

As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications, for example, labels, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands.

As used herein, "peptide", "polypeptide" and "protein" are used interchangeably and mean a compound comprising two or more amino acids linked by means of peptide bonds regardless of post-translation modification (e.g. glycosylation or phosphyorylation).

As used herein, "isolated" and "purified" are used interchangeably and mean free from other contaminating proteins, nucleic acids, and other biologicals derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and most preferably at least 99% pure. The analysis may be weight or molar percentages, and may be evaluated by any known method, e.g., by gel staining, spectrophotometry, or terminus labeling.

As used herein, the terms "complementary" or "complementarity" refer to the pairing of bases, purines and pyrimidines, that associate through hydrogen bonding in double stranded nucleic acids. For example, the following base pairs are complementary: guanine and cytosine; adenine and thymine; and adenine and uracil. The terms as used herein include complete and partial complementarity.

As used herein, "linker" means a short nucleic acid or amino acid sequence used to connect two sequences of interest. Linkers often contain enzyme cleavage sites. If more than one cleavage site is present in a linker, it is often referred to as a polylinker.

"LB medium" means Luria-Bertani medium (Sambrook et al., *Molecular Cloning*, 2nd ed. Cold Spring Harbor Laboratory Press, 1989, p. A.1; Ausubel et al., *Short Protocols in Molecular Biology*, 3rd ed., John Wiley & Sons, 1995, p. 1–3)

"IPTG" means isopropylthiogalactoside.

Amino acids are designated by standard single letter codes (Stryer, *Biochemistry*, 4th ed., W.H. Freeman & Co., 1995) where A=alanine, B=asparagine or aspartic acid, C=cysteine, D=aspartic acid, E=glutamic acid, F=phenylalanine, G=glycine, H=histidine, I=isoleucine, K=lysine, L=leucine, M=methionine, N=asparagine, P=proline, Q=glutamine, R=arginine, S=serine, T=threonine, V=valine, W=tryptophan, Y=tyrosine and Z=glutamine or glutamic acid.

DETAILED DESCRIPTION

The following detailed description is provided to aid those skilled in the art in practicing the present invention. Even so, this detailed description should not be construed to unduly limit the present invention as modifications and variation in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

The present inventors have discovered a novel method for the production of degenerate polynucleotides encoding tandem repeats of proteins or peptides using a variation of the polymerase chain reaction (PCR). In the reaction, polynucleotides encoding peptide repeats, with or without intervening sequences or linkers, serve as both primers and templates.

The novel ability to produce peptide arrays without linkers is especially useful for the production of small bioactive peptides where the addition of even a single additional amino acid can have a profound effect on biological activity.

Several potential advantages may be realized by expressing the desired protein as a tandemly ordered peptide array of cleavable protein monomeric units. By creating a tandem construct of the nucleotide sequence, it is possible to achieve a much higher proportion of recombinant protein to total protein and thereby obtain a cheaper cost of production. This is especially true in plants, since many plant storage proteins are subunits of multimeric proteins. Just reducing the number of transcription initiation events required is advantagous. Expression of large quantities of small peptides in plants can potentially present problems to the physiological health of the plant. Additionally, expression of small foreign proteins in the cell may lead to protease susceptibility. A reduction in the ability of a plant to breakdown a foreign protein, can lead to a higher yield of the protein in a transgenic plant. Applicants' method provides an efficient and effective mechanism for preventing or reducing the digestion of transgenic proteins by host proteases by expressing degenerate nucleotide sequences coding for a tandemly ordered repeat of the desired peptide in a readily producible manner. This lowers the number of kinetically available sites to protease digestions.

One type of protein which may be produced by the method of the present invention are small bioactive peptides and in particular bioactive peptides which may be used as dietary supplements in the treatment and control of hypertension. Hypertension is generally clinically defined as a systolic blood pressure greater than 140 mm Hg or a diastolic blood pressure greater than 90 mm Hg. Approximately 60 million people in the United States and 170 million people worldwide suffer from hypertension. Hypertension is the primary risk factor for coronary, cerebral, and renal vascular diseases which cause over half of all deaths in the United States. The widespread awareness of the danger of elevated blood pressure has become the most frequent reason for visits to physicians.

Dietary supplements either derived from natural sources or synthesized, as well as pharmaceutical compositions, are important to control the blood pressure of patients suffering from hypertension. Recently, a number of functional peptides derived from milk, soy, corn, gelatin, wheat, and fish protein have been identified as having functions relating to physiological regulation and angiotensin converting enzyme (ACE) inhibition. See e.g., U.S. Pat. Nos. 5,238,932 and 5,071,955. ACE catalyzes the conversion of angiotensin I to angiotensin II which increases blood pressure by contracting the smooth muscles of the blood vessel walls and promoting secretion of aldosterone by action on the adrenal cortex. ACE inhibiting substances isolated from various foods and microorganisms are being investigated for their potential as anti-hypertensive agents. (Kunio Suetsuna (1988) "Hakko to Kogyo" (Fermentation and Industry) 46:179–182). Furthermore, ACE inhibiting substances may be derived from casein and corn seed proteins (See Susumu Maruyama (1989) *Biosciences and Industry* 47:38–42; Susumu Maruyama et al. (1988) Lecture Gists for the 1988 Year Great Annual Meeting of Nippon Hakko Kogaku Kai (Japan Fermentation Engineering Society), p. 23; Susumu Maruyama et al., (1989) Lecture Gists for the 1989 Year Meeting of Nippon Nogei Kagaku Kai (*Japan Soc. Biosci. Biotechnol. Agrochem.*, p. 8; Shinsuke Miyoshi et al. (1989) Gists for the 1989 Year Meeting of Nippon Eiyo Shokuryo Gakid (Japan Nutritional and Food Society) p. 113; and Shinsuke Miyoshi et al. (1990) Nippon Nogei Kagaku Kaishi, *J. Japan Agric. Chem. Soc.*, 64(3), 555, (Lecture Gists for the 1990 Year Great Annual Meeting)) and fish meat protein from sardines, tuna and bonito (See Hiroyuki Ukeda (1992) Nippon Nogei Kagaku Kaishi, *J. Japan Soc. Biosci. Biotechnol. Agrochem.*, 66:25–29; Astawan et al. (1995) *Biosci. Biotech. Biochem.*, 59:425–429, 425). Some of these natural ACE inhibitory peptides derived from food products have been reported as effective in reducing hypertension.

Of particular interest are the peptides LKPNM (SEQ ID NO: 1), KPNM (SEQ ID NO: 2), VVYP (SEQ ID NO: 3), KPN, DKP, YKP, EKP, DAP, EAP, HPP, VPP, LK, PN and NM. LKPNM has been isolated from dried bonito digested in thermolysin. Dried bonito is a traditional Japanese seasoning made of skipjack tuna (bonito) muscle. The LKP peptide fragment exhibits the greatest anti-hypertensive properties and is therefore believed to be a principal active form of LKPNM. LKP has been isolated from digestion of fish muscle, corn protein, soybeans, and milk products. LKPN is another peptide subunit that is an enzymatic product of LKPNM and also exhibits anti-hypertensive properties. LKPN has been isolated from the enzymatic digestion of fish muscle and soybeans. See Suetsuna et al. (1991) *Kiso to Rinsho* (Clinical Report) 25: 4773–4784; Japanese Patent Application No. 7138287. Because these peptides have significant anti-hypertensive activity, they are also useful in the treatment and prophylaxis of hypertension, left ventricular systolic dysfunction, myocardial infarction, diabetes mellitus, and progressive renal impairment or failure, as well as other diseases caused by or associated with hypertension. However, most of these antihypertensive peptides are contained only in small amounts in natural products and therefore, a sufficient effect on hypertension cannot be expected in practical oral intake.

The nucleotide sequences used in the present invention should be designed to have the greatest possible variation in nucleotide sequence while still maintaining the repetitiveness of the amino acid sequences encoded. This variation greatly reduces the chance of recombination and so makes the sequences highly stable. Thus, it is preferable that nucleotide sequences used be synthesized so that the tandemly arrayed repetitive units will, to the extent possible, have different codons for the same amino acids. It is therefore preferred that not more than 95% and more preferably, not more than 90% of the nucleotide sequences encoding the repetitive units be identical. In many cases, the percent of identical nucleotide sequences will be substantially lower than 90%, for example, in one embodiment the percent identical nucleotide sequences is less than 80%, in another embodiment, less than 70%, in still another embodiment less than 60% in yet another embodiment less than 50%, in a further embodiment less than 40% and in yet another embodiment less than 25%.

The polynucleotides containing tandemly repeated sequences used in the first cycle of the PCR reaction of the present invention can be synthesized by any means known in the art. Most commonly, oligonucleotides are synthesized on a solid support using the phosphite triester method of Beaucage and Caruthers (*Tetrahedron Lett.* 22:1859–1862, 1981; also see, U.S. Pat. Nos. 4,973,679 and 4,458,066). Numerous solid supports are available including controlled pore glass beads, polystyrene copolymers, silica gel and cellulose paper. The preparation of an oligonucleotide begins with the linkage of the 3'-hydroxyl group of the first nucleoside to the solid support. Solid supports containing nucleotides are available from commercial sources. The oligonucleotide is synthesized from the 3' to 5' direction and the chain is elongated by nucleophilic attack of the 5'-hydroxyl of the immobilized oligonucleotide on the activated 3' phosphate or phosorphramidite of a soluble 5'-protected building block. The intermediate dinucleoside phosphite formed must next be oxidized to the more stable phosphate before chain extension. The process is repeated until the desired number of nucleotides has been added. Automated devices are commercially available for the synthesis of oligonucleotides. In addition, numerous commercial vendors provide custom oligonucleotide synthesis services.

The number of repeats in the polynucleotides synthesized for use in the first PCR cycle will vary with the length of the repeats and the overall length of the polynucleotide. At a minimum the sequence will be repeated at least once in the polynucleotide. Using current technology, the practical limit for the synthesis of polynucleotides by solid phase synthesis is about 100 to 120 bases. Thus for a pentapeptide, one embodiment would utilize a 120 base polynucleotide containing eight repeats of 15 nucleotides. Although the preceding example uses the maximum number of repeats under current technology, it will be apparent to those of ordinary skill in the art that shorter polynucleotides containing fewer repeats can be used in the present method. Shorter polynucleotides with fewer repeats may be constructed due to practical considerations such as the cost and difficulty of synthesis.

In synthesizing the polynucleotides, the degeneracy of the genetic code is utilized so that the greatest variation in nucleotide sequences is obtained. For example and without limitation, for the amino acid sequence LKPNM (SEQ ID NO: 1), the polynucleotide sequence would be 5'-CTN AAR CCN AAY ATG (SEQ ID NO: 4), where N is A, T, C or G; R is A or G; and Y is C or T. Using this formula, it is possible to synthesize 64 (4×2×4×2) different nucleotide sequences encoding the same amino acid sequence. If the synthesis is conducted so that four tandem repeats of the LKPNM sequence are encoded, (see Example 1), then the maximum number of different polynucleotide sequences that may be synthesized is over 16 million ($64^4$). Depending on the number of polynucleotides synthesized and because insertion of a particular nucleotide base at a location designated N, R or Y is random, not all possible polynucleotides may be represented in a given population. But even in those cases where the maximum theoretical number of polynucleotides is not reached, the variation within the population of polynucleotides will still be extremely high. Such a high degree of variation would not be possible in methods in which the sequences of the polynucleotides used to construct the repeating peptides is known, since the technological difficulties in specifically synthesizing or sequencing such a large number of different polynucleotides would make the method impractical.

The polynucleotides synthesized are extended in a series of reactions in which the 3' ends of the polynucleotides are extended in the presence of a polymerase and the four nucleotide triphosphate bases (NTPs) in a variation of the polymerase chain reaction. The reaction varies from traditional PCR in that no primers are present in the reaction mixture. Instead, the two polynucleotide strands serve as primers for their complements. Methods for conducting PCR are well known in the art. Optimization of PCR conditions can be performed by those skilled in the art without undue experimentation using the guidance provided in numerous references, for example, in Mullis et al., U.S. Pat. No. 4,683,195; Mullis, U.S. Pat. No. 4,683,202; and Innis et al., *PCR Protocols, Academic Press,* 1990; Ausubel et al., *Short Protocols in Molecular Biolgogy,* 2nd ed., Wiley & Sons, 1995, unit 15.

Suitable DNA polymerases for conducting the present invention are available from a number of commercial sources. Typically, a thermal stable DNA polymerase such as the polymerase obtained from the thermophillic bacterium *Thermus aquaticus* (Taq polymerase) or a variant of Taq polymerase is used. The concentration of NTPs used in the reaction can vary, but in general, NTPs should be in excess. Although it is normally preferable that the concentration of all four NTPs be equal in order to decrease misincorporation errors, in certain instances is may be preferable to vary from equal concentrations in situations, for example, where the sequence contains a high percentage of one or more bases.

Generally, the reaction occurs in a buffered aqueous solution, preferably with a pH between and pH 7 to pH 9 and more preferably between about pH 8.3 and 8.8 when measured at 20° C. Any suitable buffer may be used. Typically, the buffer is Tris-HCl at a concentration of between about 10 mM to 50 mM. In addition, the solution contains a divalent cation, preferably $Mg^{2+}$ ion. The magnesium should be in excess of the concentration of NTPs present, typically the solution contains 0.5 to 2.5 mM magnesium over the concentration of NTPs. In addition the reaction solution may contain up to 50 mM KCl, gelatin, bovine serum albumin or nonionic detergents.

Once all the components have been assembled in the reaction mixture, the mixture is subjected to repeated cycles of annealing, extension and denaturation. The temperature and length of time required for annealing of the polynucleotides will vary depending on the nucleotide composition, length and concentration of the polynucleotides, and can be determined by one of ordinary skill in the art without undue experimentation. The polynucleotides in the mixture will anneal such that the 3' end of one strand will serve as a primer while its complementary strand serves as the template for primer extension.

FIG. 1 depicts a representation of the process of the present invention. The synthesized polynucleotides can be combined as individual single strands or as double stranded molecules. If double stranded, the complementary strands can be denatured by any suitable method, most typically heating. Conditions are then adjusted so that the complementary single-stranded polynucleotides anneal. Because of the high degree of variability in the nucleotide sequences, it is possible that not all sequences will anneal. Rather, sequences will anneal which, by random chance, have complementary sequences. Based on probability, the most likely situation is that polynucleotides will anneal though complementary peptide repeat sequences located on their 3' and 5' ends. Less likely, is that the annealing will involve peptide repeat sequences other than those located on the ends of the polynucleotides, since the probability of two or more complementary sequences in the same order on complementary polynucleotides decreases with the number of peptide repeats involved. The fact that not all of the polynucleotides will actually anneal does not present a problem. The exponential production of product possible by using repeated chain extension reactions allows the production of large number of degenerate polynucleotides encoding proteins containing repeating units, even in situations where a low percentage of the polynucleotides actually anneal.

Following annealing, the 3' ends of the polynucleotides are extended using a suitable polymerase. Suitable polymerases include, but are not limited to, *E. coli* DNA polymerase I, Klenow fragment of *E. coli* DNA polymerase I, T4

DNA polymerase, reverse transcriptase and other suitable DNA and RNA polymerase enzymes, including heat stable enzymes. Suitable heat stable DNA polymerases include those obtained from *Thermus aquaticus, Themocuccus literalis,* and *Pyroccoccus furiosus.* Polynucleotide extension will generally begin at the 3' end of each strand and proceed in the 5' direction using the complementary polynucleotide as a template to form a double stranded molecule. The resulting product will have the same repeating structure as the original polynucleotides. Optimal times and temperatures for extension will vary with the length of the template and with the particular enzyme used. Because the length of the polynucleotides produced increases with each cycle, extension times may be increased with the number of extension steps.

After extension, the newly synthesized strands are denatured by any suitable means, typically by heating, and more typically be heating to between 95° C. to 97° C., although higher temperatures may be used. The exact conditions and time required for denaturation will vary with the length and composition of the molecules. For example, when heat denaturation is used, higher temperatures will be required for long molecules and/or those with a high CG content. The steps of annealing, extension, and denaturation are then repeated until sufficient amounts of polynucleotides of the desired length are produced. The optimization of the conditions necessary for conducting the synthesis reaction and determination of the proper number of cycles can be readily determined by one of ordinary skill in the art without undue experimentation using guidance found, for example in Innis et al., *PCR Protocols,* Academic Press, 1990, Ch. 1; and Ausubel et al., *Short Protocols in Molecular Biology,* 3rd ed., John Wiley & Sons, 1995, unit 15.1.

If the polynucleotide produced is to be used to express a recombinant protein in a transformed host, it may be desirable to include restriction enzyme cleavage sites at the end of each polynucleotide. Restriction enzyme cleavage sites can be added in a separate reaction following the cycling procedure discussed above. To accomplish this, oligonucleotide primers are designed that will anneal to the 3' end of the newly synthesized polynucleotides but whose 5' end extends beyond the polynucleotide template and contains a restriction site. Alternatively, the restriction site can be added by chemical synthesis as previously described or by blunt end ligation. Methods for the addition of restriction enzyme cleavage sites to the end of polynucleotides is well known in the art and can be found for example in Innis et al., *PCR Protocols,* Academic Press, 1990, Ch. 11 and Sambrook et al., *Molecular Cloning,* 2nd ed., Cold Spring Harbor Laboratory Press, 1989, Ch. 1.

Additionally, the end of the polynucleotide can be modified by the addition of a sequence encoding an amino acid sequence useful for purification of the protein produced by affinity chromatography. Various methods have been devised for the addition of such affinity purification moieties to proteins. Representative examples can be found in U.S. Pat. Nos. 4,703,004, 4,782,137, 4,845,341, 5,935,824, and 5,594,115. Any method known in the art for the addition of nucleotide sequences encoding purification moieties can be used including, but not limited to, those previously discussed for addition of restriction enzyme cleavage sites.

Once synthesis has been completed, the newly synthesized polynucleotides are isolated by any suitable method, for example, ethanol precipitation, and separated on the basis of size by any suitable method, for example, gel electrophoresis. Routine methods for the isolation and separation of polynucleotides are well known in the art and can be found for example in Ausubel et al., *Short Protocols in Molecular Biology,* 3rd ed., John Wiley & Sons, 1995; Davis et al., *Basic Methods in Molecular Biology,* Elsevier Science Publishing, 1986; and Sambrook et al., *Molecular Cloning,* Cold Spring Harbor Laboratory Press, 1989.

The isolated polynucleotide can then be placed into a suitable vector to transform a host cell. The vector can be either a cloning vector or an expression vector. A cloning vector is a self-replicating DNA molecule that serves to transfer a DNA segment into a host cell. The three most common types of cloning vectors are bacterial plasmids, phages, and other viruses. An expression vector is a cloning vector designed so that a coding sequence inserted at a particular site will be transcribed into mRNA and translated into a protein. Both cloning and expression vectors contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences. Various bacterial and viral origins of replication are well known to those skilled in the art and include, but are not limited to, the pBR322 plasmid origin, the 2µ plasmid origin, and the SV40, polyoma, adenovirus, VSV and BPV viral origins. Ausubel et al., ed., *Short Protocols in Molecular Biology,* 3rd ed., Wiley & Sons, 1995.

One commonly used type of cloning vector is derived from filamentous phages, and in particular, the ϕX174 and the M13 phages. The advantage of filamentous phage vectors is that DNA inserted into them can be recovered in both the double-stranded and single stranded forms. As typically used, the nucleotide sequence to be cloned is inserted into double-stranded vector and the vector containing the sequence is introduced into cells by transformation. In the case of the M13 phage, the foreign sequence is inserted into a polylinker located in a non-essential region of the M13 genome. Cells containing vectors with filamentous phage origins, usually the f1 origin, are also infected with helper phage. The helper phage provides the gene 2 protein that drives the vector into the f1 mode of replication and the DNA packaging and export functions. Once inside the cells, the double-stranded DNA replicates and produces both new double-stranded circles and single-stranded circles. Single-stranded circles are packaged into phage coats and secreted into the medium without lysis of the host cell. Because only the (+) strand is packaged efficiently, only foreign DNA that is in the same 5'→3' orientation as the phage (+) strand origin will be packaged. Methods for the use of filamentous phage vectors are well known in the art and can be found, for example, in Ausubel et al., *Short Protocols in Molecular Biology,* 3rd ed., John Wiley & Sons, pp. 1-24–1-27, 1995 and Messing (1983) *Meth. in Enzymol.,* 101:20–79.

The polynucleotide sequence of the present method may be used to produce proteins by the use of recombinant expression vectors containing the sequence. Suitable expression vectors include chromosomal, non-chromosomal and synthetic DNA sequences, for example, SV 40 derivatives; bacterial plasmids; phage DNA; baculovirus; yeast plasmids; vectors derived from combinations of plasmids and phage DNA; and viral DNA such as vaccinia, adenovirus, fowl pox virus, and pseudorabies. Vectors for plant transformation have been reviewed in Rodriguez et al. (1988) *Vectors: A Survey of Molecular Cloning Vectors and Their Uses,* Butterworths, Boston; Glick et al. (1993) *Methods in Plant Molecular Biology and Biotechnology* CRC Press, Boca Raton, Fla.; and Croy (1993) In *Plant Molecular*

Biology Labfax, Hames and Rickwood, Eds., BIOS Scientific Publishers Limited, Oxford, UK. In addition, any other vector that is replicable and viable in the host may be used.

The nucleotide sequence of interest may be inserted into the vector by a variety of methods. In the most common method, the sequence is inserted into an appropriate restriction endonuclease site(s) using procedures commonly known to those skilled in the art and detailed in, for example, Sambrook et al., *Molecular Cloning, A Laboratory Manual*, 2nd ed., Cold Spring Harbor Laboratory Press, (1989) and Ausubel et al., *Short Protocols in Molecular Biology*, 3rd ed., John Wiley & Sons (1995).

In an expression vector, the sequence of interest is operably linked to a suitable expression control sequence or promoter recognized by the host cell to direct mRNA synthesis. Promoters are untranslated sequences located generally 100 to 1000 base pairs (bp) upstream from the start codon of a structural gene that regulate the transcription and translation of nucleic acid sequences under their control. Promoters are generally classified as either inducible or constitutive. Inducible promoters are promoters that initiate increased levels of transcription from DNA under their control in response to some change in the environment, e.g. the presence or absence of a nutrient or a change in temperature. Constitutive promoters, in contrast, maintain a relatively constant level of transcription. In addition, useful promoters can also confer appropriate cellular and temporal specificity. Such promoters include those that are developmentally-regulated or organelle-, tissue- or cell-specific.

A nucleic acid sequence is operably linked when it is placed into a functional relationship with another nucleic acid sequence. For example, DNA for a presequence or secretory leader is operatively linked to DNA for a polypeptide if it is expressed as a preprotein which participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading phase. Linking is achieved by ligation at restriction enzyme sites. If suitable restriction sites are not available, then synthetic oligonucleotide adapters or linkers can be used as is known to those skilled in the art. Sambrook et al., *Molecular Cloning, A Laboratory Manual*, 2nd ed., Cold Spring Harbor Laboratory Press, (1989) and Ausubel et al., *Short Protocols in Molecular Biology*, 3rd ed., John Wiley & Sons (1995).

Common promoters used in expression vectors include, but are not limited to, LTR or SV40 promoter, the *E. coli* lac or trp promoters, and the phage lambda PL promoter. Sambrook et al., *Molecular Cloning, A Laboratory Manual*, 2nd ed., Cold Spring Harbor Laboratory Press, (1989) and Ausubel et al., *Short Protocols in Molecular Biology*, 3rd ed., John Wiley & Sons (1995). In plants, often-used constitutive promoters include the CaMV 35S promoter (Odell et al. (1985) *Nature* 313: 810), the enhanced CaMV 35S promoter, the Figwort Mosaic Virus (FMV) promoter (Richins et al. (1987) *NAR* 20: 8451), the mannopine synthase (mas) promoter, the nopaline synthase (nos) promoter, and the octopine synthase (ocs) promoter.

Useful inducible plant promoters include heat-shock promoters (Ou-Lee et al. (1986) *Proc. Natl. Acad. Sci. USA* 83: 6815; Ainley et al. (1990) *Plant Mol. Biol.* 14: 949), a nitrate-inducible promoter derived from the spinach nitrite reductase gene (Back et al. (1991) *Plant Mol. Biol.* 17: 9), hormone-inducible promoters (Yamaguchi-Shinozaki et al. (1990) *Plant Mol. Biol.* 15: 905; Kares et al. (1990) *Plant Mol. Biol.* 15: 905), and light-inducible promoters associated with the small subunit of RuBP carboxylase and LHCP gene families (Kuhlemeier et al. (1989) *Plant Cell* 1: 471; Feinbaum et al. (1991) *Mol. Gen. Genet.* 226: 449; Weisshaar et al. (1991) *EMBO J.* 10: 1777; Lam and Chua (1990) *Science* 248: 471; Castresana et al. (1988) *EMBO J.* 7: 1929; Schulze-Lefert et al. (1989) *EMBO J.* 8: 651).

Examples of tissue-specific, developmentally-regulated promoters in plants include fruit-specific promoters such as the E4 promoter (Cordes et al. (1989) *Plant Cell* 1:1025), the E8 promoter (Deikman et al. (1988) *EMBO J.* 7: 3315), the kiwifruit actinidin promoter (Lin et al. (1993) *PNAS* 90: 5939), the 2A11 promoter (Houck et al., U.S. Pat. No. 4,943,674), and the tomato pZ130 promoter (U.S. Pat. Nos. 5,175,095 and 5,530,185); the β-conglycinin 7S promoter (Doyle et al. (1986) *J. Biol. Chem.* 261: 9228; Slighton and Beachy (1987) *Planta* 172: 356), and seed-specific promoters (Knutzon et al. (1992) *Proc. Natl. Acad. Sci. USA* 89: 2624; Bustos et al. (1991) *EMBO J.* 10: 1469; Lam and Chua (1991) *J. Biol. Chem.* 266: 17131; Stayton et al. (1991) *Aust. J. Plant. Physiol.* 18: 507). Fruit-specific gene regulation is discussed in U.S. Pat. No. 5,753,475. Other useful seed-specific promoters include, but are not limited to, the napin, phaseolin, zein, soybean trypsin inhibitor, 7S, ADR12, ACP, stearoyl-ACP desaturase, oleosin, Lasquerella hydroxylase, and barley aldose reductase promoters (Bartels (1995) *Plant J.* 7: 809–822), the EA9 promoter (U.S. Pat. No. 5,420,034), and the Bce4 promoter (U.S. Pat. No. 5,530,194). Useful embryo-specific promoters include the corn globulin 1 and oleosin promoters. Useful endosperm-specific promoters include the rice glutelin-1 promoter, the promoters for the low-pI α-amylase gene (Amy32b) (Rogers et al. (1984) *J. Biol. Chem.* 259: 12234), the high-pI α-amylase gene (Amy 64) (Khurseed et al. (1988) *J. Biol. Chem.* 263: 18953), and the promoter for a barley thiol protease gene ("Aleurain") (Whittier et al. (1987) *Nucleic Acids Res.* 15: 2515). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al. (1991) *Seed Sci. Res.* 1: 209), phaseolin, zein, soybean trypsin inhibitor, ACP, stearoyl-ACP desaturase, and oleosin. Seed-specific gene regulation is discussed in EP 0 255 378 B1 and U.S. Pat. Nos. 5,420,034 and 5,608,152. Promoter hybrids can also be constructed to enhance transcriptional activity (Hoffman, U.S. Pat. No. 5,106,739), or to combine desired transcriptional activity and tissue specificity.

Other promoters known to control the expression of genes in prokaryotic or eukaryotic cells can be used and are known to those skilled in the art. For example, the casein promoter can be used to direct expression of the foreign protein into the milk. Expression vectors may also contain a ribosome binding site for translation initiation, and a transcription terminator. The vector may also contain sequences useful for the amplification of gene expression.

Expression and cloning vectors can, and usually do, contain a selection gene or selection marker. Typically, this gene encodes a protein necessary for the survival or growth of the host cell transformed with the vector. Examples of suitable selection markers include dihydrofolate reductase (DHFR) or neomycin resistance for eukaryotic cells and tetracycline or ampicillin resistance for *E. coli*. Selection markers in plants have include bleomycin, gentamycin, glyphosate, hygromycin, kanamycin, methotrexate, phleomycin, phosphinotricin, spectinomycin, dtreptomycin, sulfonamide and sulfonylureas resistance. Maliga et al., *Methods in Plant Molecular Biology*, Cold Spring Harbor Laboratory Press, 1995, p. 39.

In addition, expression vectors can also contain marker sequences operatively linked to a nucleotide sequence for a protein that encode an additional protein used as a marker. The result is a hybrid or fusion protein comprising two linked and different proteins. The marker protein can provide, for example, an immunological or enzymatic marker for the recombinant protein produced by the expression vector. Suitable markers include, but are not limited to, alkaline phosphatase (AP), myc, hemagglutinin (HA), β-glucuronidase (GUS), luciferase, and green fluorescent protein (GFP).

The polynucleotide sequences of the present invention can also be part of an expression cassette that at a minimum comprises, operably linked in the 5' to 3' direction, a promoter, a polynucleotide of the present invention, and a transcriptional termination signal sequence functional in a host cell. The promoter can be of any of the types discussed herein, for example, a tissue specific promoter, a developmental regulated promoter, an organelle specific promoter, a seed specific promoter, a plastid specific promoter, etc. The expression cassette can further comprise an operably linked targeting, transit or secretion peptide coding region capable of directing transport of the protein produced. The expression cassette can also further comprise a nucleotide sequence encoding a selectable marker and a purification moiety. In addition, the expression cassette can further comprise an additional sequence encoding an enzyme capable of cleaving the polypeptide of the present invention between the tandem repeats in order to produce non-repeating peptide units. The enzyme encoding sequence can be under the control of a separate promoter, for example an inducible or developmentally regulated promoter so that production of the enzyme is triggered only after substantial amounts of the repeating polypeptide of the present invention has been produced.

More particularly, the present invention includes recombinant constructs comprising an isolated polynucleotide sequence of the present invention. The constructs can include a vector, such as a plasmid or viral vector, into which the sequence of the present invention has been inserted, either in the forward or reverse orientation. The recombinant construct further comprises regulatory sequences, including for example, a promoter operatively linked to the sequence. Large numbers of suitable vectors and promoters are known to those skilled in the art and are commercially available.

A further embodiment of the present invention relates to transformed host cells containing constructs comprising the polynucleotide sequence of the present invention. The host cell can be a higher eukaryotic cell, such as a plant or animal cell, or a lower eukaryotic cell such as a yeast cell, or the host can be a prokaryotic cell such as a bacterial cell. Introduction of the construct into the host cell can be accomplished by a variety of methods including calcium phosphate transfection, DEAE-dextran mediated transfection, Polybrene, protoplast fusion, liposomes, direct microinjection into the nuclei, scrape loading, and electroporation. In plants, a variety of different methods can be employed to introduce transformation/expression vectors into plant protoplasts, cells, callus tissue, leaf discs, meristems, etc., to generate transgenic plants. These methods include, for example, *Agrobacterium*-mediated transformation, particle gun delivery, microinjection, electroporation, polyethylene glycol-mediated protoplast transformation, liposome-mediated transformation, etc. (reviewed in Potrykus (1991) *Annu. Rev. Plant Physiol. Plant Mol. Biol.* 42: 205). Transgenic animals can be produced by the injection of the polynucleotides of the present invention into the pronucleus of a fertilized oocyte, by transplantation of cells, preferably undifferentiated cells, into a developing embryo to produce a chimeric embryo, transplantation of a nucleus from a recombinant cell into an enucleated embryo or activated oocyst, or by any other method capable of producing a transgenic animal. Methods for the production of transgenic animals can be found in a number of references including, for example, U.S. Pat. No. 4,873,191; Rudolph (1999) *Trends Biotechnol.*, 17:367–374; Dalrymple et al. (1998) *Biotechnol. Genet. Eng. Rev.*, 15:33–49; Colman (1998) *Biochem. Soc. Symp.*, 63:141–147; Perry et al. (1993) *Transgenic Res.*, 2:125–133; Hogan et al., *Manipulating the Mouse Embryo,* 2nd ed., Cold Spring Harbor Laboratory Press, 1994; and references cited therein. Gametes, seeds, embryos, progeny and hybrids of plants or animals containing polynucleotides of the present invention or producing proteins of the present invention produced by traditional breeding methods are also included within the scope of the present invention.

Also included are plants containing polynucleotides or proteins of the present invention which are apomictic. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucellus, 2) diplospory where the embryo develops from an unreduced egg in an embryo sac derived from the megaspore mother cell, and 3) adventitious embryony where the embryo develops directly from a somatic cell. In most forms of apomixis, psuedogamy or fertilization of the polar nuclei to produce endosperm is necessary for seed viability. In apospory, a "nurse" cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636 and references cited therein.

Proteins produced by expression of the polynucleotides of the present invention can be obtained by transforming a host cell by any of the previously described methods, growing the host cell under appropriate conditions, inducing expression of the polynucleotide and isolating the protein(s) of interest. If the protein in retained within the host cell, the protein can be obtained by lysis of the host cells while if the protein is a secreted protein, it can be isolated from the culture medium. Several methods are available for purification of proteins and are known to those of ordinary skill in the art. These include precipitation by, for example, ammonium sulfate or ethanol, acid extraction, anion or cation exchange chromatography, phosphocellulose chromatography, hydrophobic interaction chromatography, affinity chromatography, hydroxylapatite chromatography, lectin chromatography, high performance liquid chromatography (HPLC), electrophoresis under native or denaturing conditions, isoelectric focusing, and immunoprecipitation.

In general, transgenic plants comprising cells containing polynucleotides of the present invention can be produced by any of the foregoing methods; selecting plant cells that have been transformed on a selective medium; regenerating plant cells that have been transformed to produce differentiated plants; and selecting a transformed plant that expresses the protein(s) encoded by the polynucleotides of the present invention at a desired level. Specific methods for transforming a wide variety of dicots and obtaining transgenic plants are well documented in the literature (Gasser and Fraley (1989) *Science* 244: 1293; Fisk and Dandekar (1993) *Scientia Horticulturae* 55: 5; Christou (1994) *Agro Food Industry Hi Tech*, p. 17; and the references cited therein).

Successful transformation and plant regeneration have been achieved in a variety of monocots. Specific examples are as follows: asparagus (*Asparagus officinalis*; Bytebier et al. (1987) *Proc. Natl. Acad. Sci. USA* 84: 5345); barley (*Hordeum vulgarae*; Wan and Lemaux (1994) *Plant Physiol.* 104: 37); maize (*Zea mays*; Rhodes et al. (1988) *Science* 240: 204; Gordon-Kamm et al. (1990) *Plant Cell* 2: 603; Fromm et al. (1990) *Bio/Technology* 8: 833; Koziel et al. (1993) *Bio/Technology* 11: 194); oats (*Avena sativa*; Somers et al. (1992) *Bio/Technology* 10: 1589); orchardgrass (*Dactylis glomerata*; Horn et al. (1988) *Plant Cell Rep.* 7: 469); rice (*Oryza sativa*, including indica and japonica varieties; Toriyama et al. (1988) *Bio/Technology* 6: 10; Zhang et al. (1988) *Plant Cell Rep.* 7: 379; Luo and Wu (1988) *Plant Mol. Biol. Rep.* 6: 165; Zhang and Wu (1988) *Theor. Appl. Genet.* 76: 835; Christou et al. (1991) *Bio/Technology* 9: 957); rye (*Secale cereale*; De la Pena et al. (1987) *Nature* 325: 274); sorghum (*Sorghum bicolor*; Cassas et al. (1993) *Proc. Natl. Acad. Sci. USA* 90: 11212); sugar cane (*Saccharum* spp.; Bower and Birch (1992) *Plant J.* 2: 409); tall fescue (*Festuca arundinacea*; Wang et al. (1992) *Bio/Technology* 10: 691); turfgrass (*Agrostis palustris*; Zhong et al. (1993) *Plant Cell Rep.* 13: 1); and wheat (*Triticum aestivum*; Vasil et al. (1992) *Bio/Technology* 10: 667; Weeks et al. (1993) *Plant Physiol.* 102: 1077; Becker et al. (1994) *Plant J.* 5: 299).

The recombinant proteins of the present invention can be modified for plastid targeting by employing plant cell nuclear transformation constructs wherein DNA coding sequences of interest are fused to any of the available transit peptide sequences capable of facilitating transport of the encoded proteins into plant plastids, and driving expression by employing an appropriate promoter such as any of those discussed above. Targeting of proteins to plastids can be achieved by fusing DNA encoding plastid, e.g., chloroplast, leucoplast, amyloplast, etc., transit peptide sequences to the ends of the polynucleotides of the present invention. The sequences that encode a transit peptide region can be obtained, for example, from plant nuclear-encoded plastid proteins, such as the small subunit (SSU) of ribulose bisphosphate carboxylase. Plastid transit peptide sequences can also be obtained from nucleic acid sequences encoding carotenoid biosynthetic enzymes, such as GGPP synthase, phytoene synthase, and phytoene desaturase. Other transit peptide sequences useful in the present invention are disclosed in Von Heijne et al. (1991) *Plant Mol. Biol. Rep.* 9: 104; Clark et al. (1989) *J. Biol. Chem.* 264: 17544; della-Cioppa et al. (1987) *Plant Physiol.* 84: 965; Romer et al. (1993) *Biochem. Biophys. Res. Commun.* 196: 1414; and Shah et al. (1986) *Science* 233: 478. Polypeptides of the present invention can utilize native or heterologous transit peptides. The encoding sequence for a transit peptide effective in transport to plastids can include all or a portion of the encoding sequence for a particular transit peptide, and may also contain portions of the mature protein encoding sequence associated with a particular transit peptide.

Numerous examples of transit peptides that can be used to deliver target proteins into plastids exist, and the particular transit peptide encoding sequences useful in the present invention are not critical as long as delivery into a plastid is obtained. This technique has proven successful with enzymes involved in polyhydroxyalkanoate biosynthesis (Nawrath et al. (1994) *Proc. Natl. Acad. Sci. USA* 91: 12760), neomycin phosphotransferase II (NPT-II) and CP4 EPSPS (Padgette et al. (1995) *Crop Sci.* 35: 1451), for example.

Exact translational fusions to the transit peptide of interest may not be optimal for protein import into the plastid. By creating translational fusions to the precursor form of a naturally imported protein or C-terminal deletions thereof, one would expect that such translational fusions would aid in the uptake of the engineered precursor protein into the plastid. For example, Nawrath et al. ((1994) *Proc. Natl. Acad. Sci. USA* 91: 12760) used a similar approach to create the vectors employed to introduce the polyhydroxybutyrate biosynthesis genes of *A. eutrophus* into *Arabidopsis*.

Alternatively, polypeptides encoded by the polynucleotides of the present invention can be expressed in situ in plastids by direct transformation of these organelles with appropriate recombinant expression constructs. Constructs and methods for stably transforming plastids of higher plants are well known in the art (Svab et al. (1990) *Proc. Natl. Acad. Sci. USA* 87: 8526; Svab et al. (1993) *Proc. Natl. Acad. Sci. USA* 90: 913; Staub et al. (1993) *EMBO J.* 12: 601; Maliga et al., U.S. Pat. No. 5,451,513; Maliga et al., PCT International Publications WO 95/16783, WO 95/24492, and WO 95/24493; and Daniell et al., U.S. Pat. No. 5,693,507). These methods generally rely on particle gun delivery of DNA containing a selectable marker in addition to introduced DNA sequences for expression, and targeting of the DNA to the plastid genome through homologous recombination. Transformation of a wide variety of different monocots and dicots by particle gun bombardment is routine in the art (Hinchee et al. (1994) In: *Plant Cell and Tissue Culture*, I. Vasil and T. Thorpe (Eds.), Kluwer Academic Publishers, Netherlands, p. 231; Walden and Wingender (1995) *TIBS* 13: 324).

DNA constructs for plastid transformation generally comprise a targeting segment comprising flanking DNA sequences substantially homologous to a predetermined sequence of a plastid genome, which targeting segment enables insertion of DNA coding sequences of interest into the plastid genome by homologous recombination with the predetermined sequence; a selectable marker sequence, such as a sequence encoding a form of plastid 16S ribosomal RNA that is resistant to spectinomycin or streptomycin, or that encodes a protein which inactivates spectinomycin or streptomycin (such as the aadA gene), disposed within the targeting segment, wherein the selectable marker sequence confers a selectable phenotype upon plant cells, substantially all the plastids of which have been transformed with the DNA construct; and one or more DNA coding sequences of interest disposed within the targeting segment relative to the selectable marker sequence so as not to interfere with conferring of the selectable phenotype. In addition, plastid expression constructs also generally include a promoter region functional in a plant plastid and a transcription termination region capable of terminating transcription in a plant plastid, wherein these regions are operatively linked to the DNA coding sequences of interest.

A further refinement in chloroplast transformation/expression technology that facilitates control over the timing and tissue pattern of expression of introduced DNA coding sequences in plant plastid genomes has been described in PCT International Publication WO 95/16783 and U.S. Pat. No. 5,576,198. This method involves the introduction into plant cells of constructs for nuclear transformation that provide for the expression of a viral single subunit RNA polymerase and targeting of this polymerase into the plastids via fusion to a plastid transit peptide. Transformation of plastids with DNA constructs comprising a viral single subunit RNA polymerase-specific promoter specific to the RNA polymerase expressed from the nuclear expression constructs operably linked to DNA coding sequences of interest permits control of the plastid expression constructs in a tissue and/or developmental specific manner in plants comprising both the nuclear polymerase construct and the plastid expression constructs. Expression of the nuclear RNA polymerase coding sequence can be placed under the control of either a constitutive promoter, or a tissue- or developmental stage-specific promoter, thereby extending this control to the plastid expression construct responsive to the plastid-targeted, nuclear-encoded viral RNA polymerase. The introduced DNA coding sequence can be a single encoding region, or may contain a number of consecutive encoding sequences to be expressed as an engineered or synthetic operon.

Although typically used to produce bioactive peptides and proteins, the method of the present invention can be used to produce polynucleotide sequences encoding amino acid sequences with a high percentage of a particular amino acid. The expression of these sequences within, for example, a transgenic plant, can be used to alter the amino acid profile of the plant. In one preferred embodiment, at least 25% of the codons in the sequence encode the desired amino acid. In another preferred embodiment, at least 50% of the codons encode the desired amino acid, and in yet another preferred embodiment, at least 75% of the codons encode the desired amino acid. In still another preferred embodiment, at least 90% of the codons encode the preferred amino acid.

Proteins produced by the method of the present invention can have therapeutic or nutritional value. The isolated proteins of the present invention can be administered by any means known in the art. When the proteins of the present invention are formulated as therapeutic or pharmaceutical compositions, such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrastemal injection, or infusion techniques. Formulation of drugs is discussed in, for example, Hoover, John E., *Remington's Pharmaceutical Sciences*, Mack Publishing Co., Easton, Pa. (1975), and Liberman, H. A. and Lachman, L., Eds., *Pharmaceutical Dosage Forms*, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compositions discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

The proteins of the present invention can also be administered in a non-isolated form to provide therapeutic or nutritional value to a subject. For example, when the proteins are produced by transgenic plants or animals containing a polynucleotide of the present invention, the protein can be administered by consumption of the plant or animal itself, or a product of the transgenic plant or animal. Examples of products that may be consumed in order to administer the proteins of the present invention include, but are not limited to, fruits, vegetables, flours, meals, powders, juices, oils, seeds, extracts, eggs, milk, or any consumable item made from the aforementioned products.

EXAMPLES

The following examples are intended to provide illustrations of the application of the present invention. The following examples are not intended to completely define or otherwise limit the scope of the invention.

Example 1

Production of Polynucleotides Containing Repeated Sequences

A pool of polynucleotides encoding four repeats of the amino acid sequence LKPMN (SEQ ID NO: 1), without any intervening sequence between the repeats, and their complements were synthesized using an automated variation of the method for the synthesis of oligonucleotides described previously. The sequences of the forward and reverse strands, respectively, were as follows:
L  K  P  M  N
5'-CTN AAR CCN AAY ATG CTN AAR CCN AAY ATG CTN AAR CCN AAY ATG CTN AAR CCN AAY ATG-3' (SEQ ID NO:5)
5'-CAT RTT NGG YTT NAG CAT RTT NGG YTT NAG CAT RTT NGG YTT NAG CAT RTT NGG YTT NAG-3' (SEQ ID NO: 6)

where N=any nucleotide, R=A or G, and Y=C or T.

Two hundred pmoles each, of forward and reverse polynucleotides were self-assembled into varying sizes of polynucleotides using the present method of the present invention. In addition to the polynucleotides, the reaction mix contained 0.75 µl of enzyme mix, 5 µl 10× buffer with MgCl$_2$, and 1 µl of 10 mM dNTP (Roche Molecular Biochemicals, Indianapolis, Ind., Cat. # 1732641). The final volume of the reaction mixture was brought to 50 µl with water. No additional template or primer in addition to the synthesized 60-mer polynucleotides were used in the reaction. The reaction was carried out in a programable thermocycler programed as follows: 94° C. for 2 minutes followed by 10 cycles of 94° C. for 15 seconds, 50° C. for 30 seconds, and 72° C. for 30 seconds; followed by 20 cycles of 94° C. for 15 seconds, 50° C. for 30 seconds, 72° C. for 45 s plus 5 seconds/cycle; followed by a hold at 4° C. If amplification was to proceed beyond 30 cycles, after each multiple of 30 cycles an additional 0.5 µl of fresh enzyme mix was added to each reaction.

Following the reaction, the reaction products were isolated and separated by electrophoresis on a 1% agarose gel using standard techniques for the isolation and separation of PCR products. Ausubel et al., *Short Protocols in Molecular Biology*, 3rd ed., John Wiley & Sons, 1995; Davis et al., *Basic Methods in Molecular Biology*, Elsevier Science Publishing, 1986; and Sambrook et al., *Molecular Cloning*, 2nd ed., Cold Spring Harbor Laboratory Press, 1989.

The results can be seen in FIG. 2. Prior to conducting the reaction, (0 cycles) a single band representing the synthesized 60-mer polynucleotides was observed (lane 1). After 30 cycles, however, a smear of DNA between about 80 to 200 bp was observed (lane 2). After 60 cycles, DNA between about 100 and 600 bp was observed (lane 3). The increase in polynucleotide size reached a plateau after 60 cycles (lane 4, 90 cycles). This plateau is thought not to represent the limit of the size of the polynucleotides that may be synthesized using the present method, but rather, indicate the need to alter reaction conditions as the polynucleotides produced become longer.

Example 2

Introduction of Restriction Site to the Ends of the Synthesized Polynucleotides and Transformation of Host Cells Polynucleotides of approximately 100 to 600 bp produced in Example 1 (FIG. 2, lane 3) were isolated from the agarose gel and subjected to standard PCR in order to add restriction sites to the ends of the polynucleotides produced. The primers used were as follows:
5'-AAAGAATTCCTNAARCCNAAYATGC-3' (SEQ ID NO: 7)
5'-AAAGCGGCCGCCATRTTNGGYTTNAGC-3' (SEQ ID NO: 8).

Figure 3:
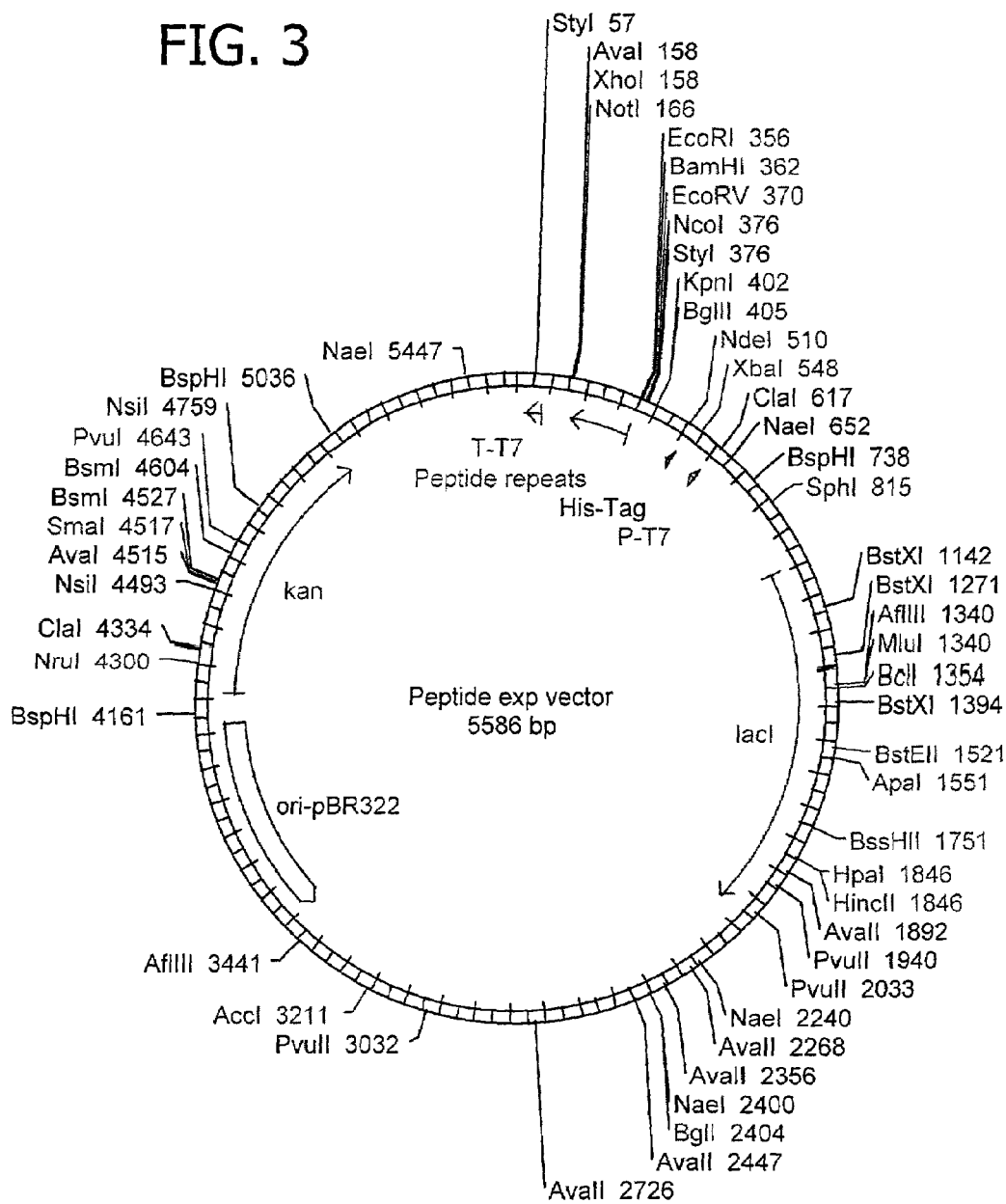
FIG. 3 shows the pET30(a)+ expression vector used to produce peptides by the present method.

Instead of the forward and reverse polynucleotides of Example 1, the PCR reaction mix contained approximately 30 ng of product from Example 1 and 100 pmoles of each primer. The remainder of the reaction mix was the same as in Example 1. The thermal cycle program was the same as in Example 1, except that the annealing temperature was 40° C. instead of 50° C. The products of the PCR reaction were isolated and separated on 1% agarose cells using standard techniques and the products between 300–600 bp isolated from the gel. The DNA was digested with NotI and EcoRI restriction enzymes and ligated in frame into pET30a(+) expression vectors (FIG. 3). The vectors were then used to transform *E. coli* BL21 DE3, the companion host organism for the pet30 *E. coli* expression system. Standard methods for insertion of the polynucleotide into the expression vector and transformation of the host cell were used. Ausubel et al., *Short Protocols in Molecular Biology*, 3rd ed., John Wiley & Sons, 1995; Davis et al., *Basic Methods in Molecular Biology*, Elsevier Science Publishing, 1986; and Sambrook et al., *Molecular Cloning*, 2nd ed., Cold Spring Harbor Laboratory Press, 1989. Five colonies of BL21 DE3 were tested for the presence of the inserted polynucleotide. The presence of the polynucleotide was determined using PCR. The primers used were as follows:
5'-TAATACGACTCACTATAGGG-3' (SEQ ID NO: 9)
5'-CGATCAATAACGAGTCGCC-3' (SEQ ID NO: 10)

Figure 4:
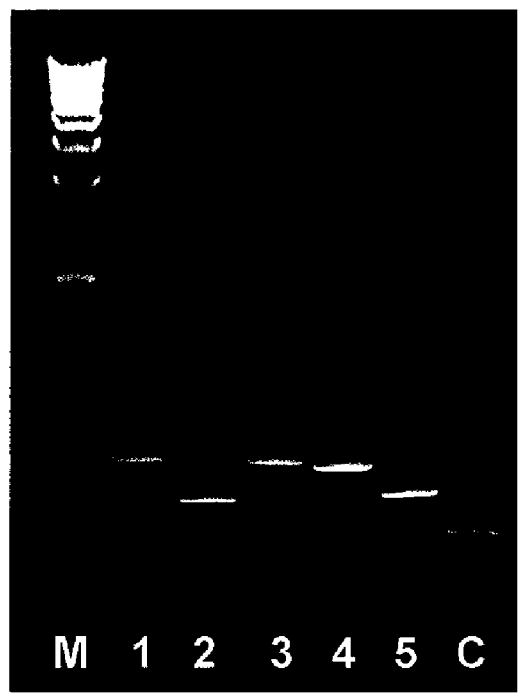
FIG. 4 shows an agarose gel of PCR products obtained from five colonies (Lanes 1–5) of E. coli BL21 DE3 transformed with polynucleotides of the present method. Lane M contains size markers while Lane C contains PCR products from bacteria transformed with vector not containing polynucleotide inserts.

The reaction conditions were the same as those used to introduce restriction sites. Amplification products were visualized on 1% agarose gels as in Example 1. The results are shown in FIG. 4. All five colonies tested were found to contain inserts (lanes 1–5) when compared to pET30a(+) vector alone (lane C).

Example 3

Expression of the Recombinant Proteins by the Host Cells

Figure 5:
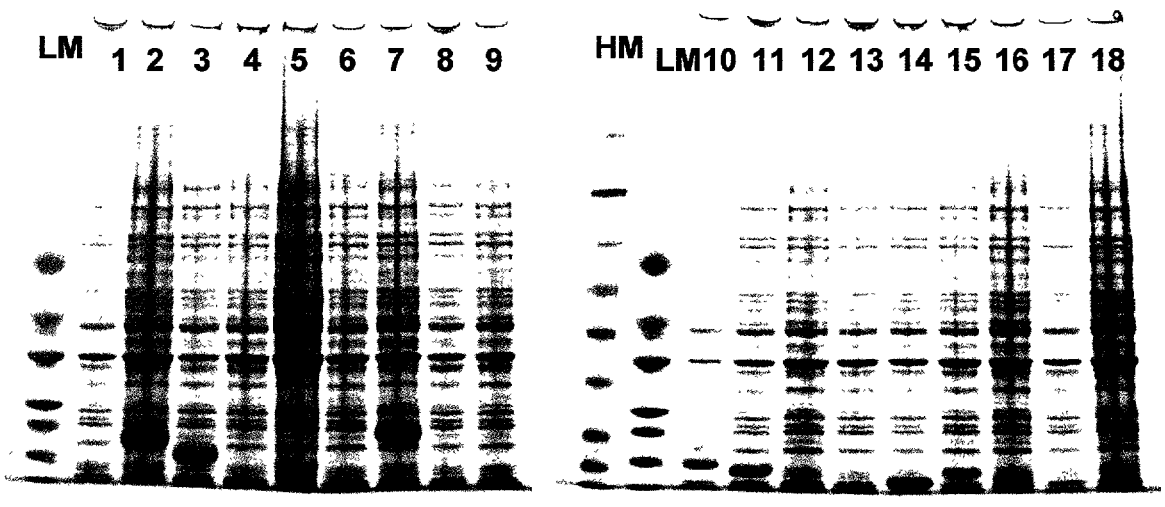
FIG. 5 shows an SDS-PAGE gel of extracts from *E. coli* BL21 DE3 transformed with the polynucleotides of the present method and induced to express the encoded polypeptides. Numbered lanes represent different cultures. HM and LM represent high and low molecular weight markers, respectively.
Figure 6:
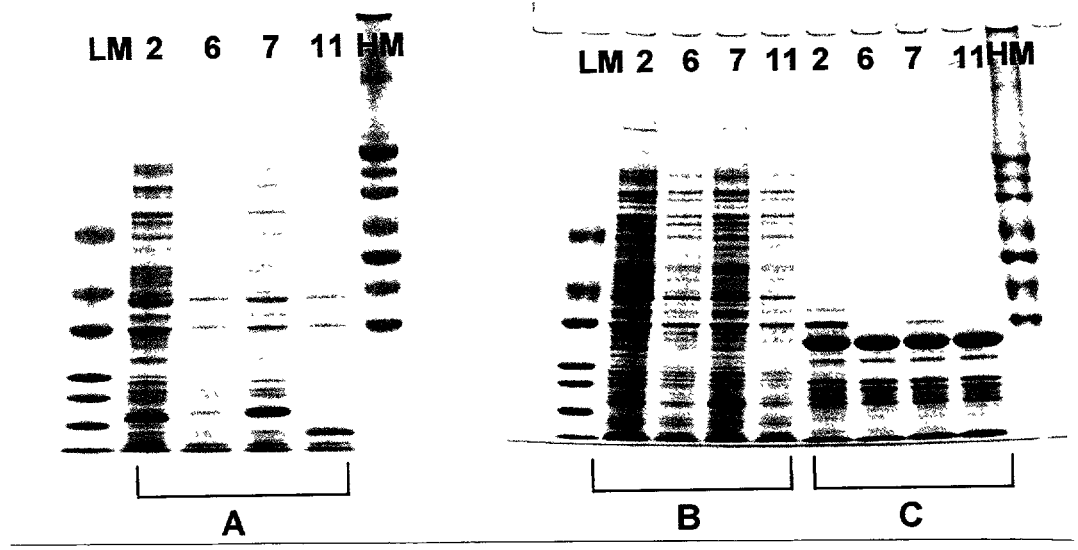
FIG. 6A shows an SDS-PAGE gel of aqueous extracts from cultures 2, 6, 7 and 11 of *E. coli* BL21 DE3 transformed with the polynucleotides of the present method and induced to express the encoded polypeptides. HM and LM are the same as in FIG. 5.
FIG. 6B shows the same extract as in FIG. 6A after incubation at 37° C. for 3 hours.
FIG. 6C shows the same extract as in FIG. 6A after digestion with thermolysin.

To test for expression of the inserted polynucleotides of the present method, transformed BL21 DE3 colonies were inoculated into 1 ml of LB medium and grown at 37° C. for 3 hours. After the 3 hour growth period, protein expression was induced by addition of IPTG to a final concentration of 1 mM followed by an additional 2 hour incubation at 37° C. After induction, 400 µl of the culture medium was collected and pelleted. The pellet was resuspended in 1× SDS loading buffer (50 mM Tris-HCl, pH 6.8, 100 mM dithiotheritol, 2% sodium dodecyl sulfate, 10% glycerol) and a 12 μl sample loaded onto a 4%–20% gradient SDS-PAGE gel. The results are shown in FIG. 5. Among the 18 colonies tested, clones 2, 7, and 11 (lanes 2, 7, & 11) were chosen as positive expressers and clone 6 (lane 6) was chosen as a non-expresser. To test if the polypeptide produced was water soluble, another sample from the same culture was pelleted, resuspended in 25 mM Tris (pH 7.0) and sonicated. After centrifugation, the supernatant was mixed with 2× SDS loading buffer, boiled and loaded onto a 4%–20% gradient SDS-PAGE gel. The results are shown in FIG. 6A and show that the polypeptide was soluble in 25 mM Tris buffer. The specific band in lanes 2 and 11 disappeared after incubation of the supernatant alone at 37° C. for 3 hours, suggesting that the polypeptide was susceptible to endogenous proteases (FIG. 6B). Addition of thermolysin to the sample resulted in the disappearance of the specific bands in all three positive samples (FIG. 6C).

Example 4

Sequence of Polynucleotides in Clones

DNA from clones 2, 6, 7 and 11 was isolated and sequenced using standard methods. Sequencing was accomplished by a variation of the dideoxy method of Sanger et al., *Proc. Natl. Acad. Sci. USA*, 74:5463–5467 (1977) using an ABI Prism™ automatic sequencer (PE Biosystems, Foster City, Calif.) using the manufacturer's protocols. The sequence data obtained is presented in FIG. 7A with the corresponding deduced protein sequences given in FIG. 7B. All sequences were trimmed so that only the LKPNM coding region was retained. Although most clones had DNA inserts, only about one-third of the clones produced measurable amounts of peptide. This was confirmed by the sequencing data where clone 6 did not produce measurable amounts of the LKPNM peptide, although an insert was present. Clones 2 and 11 were found to have an A to T substitution mutation shown in bold in FIG. 7A. These mutations may have been due to either PCR mutations or synthesizer error. The substitution resulted in a leucine (L) being substituted for a methionine (M) as shown by the bold type in FIG. 7B. The sizes of the peptides determined from the sequencing data were consistent with the sizes of the peptides observed by gel electrophoresis.

Example 5

Cleavage of the Recombinant Polypeptide

The ability of thermolysin to release the individual LKPNM peptides from the polypeptide is shown by this example. A 5 ml culture of each of clones 2, 6, 7 and 11 was prepared as in Example 3. A clone transformed with pET 30a(+) not containing the polynucleotide insert was included as a negative control. Cells from each 5 ml culture were pelleted and extracted in 25 mM Tris (pH 7.0) and centrifuged. Extracts were heat-treated at 95° C. for 10 minutes to inactivate endogenous proteases. One ml of supernatant was collected and thermolysin added to cleave the LKPNM repeats of the polypeptide. Thermolysin treatment consisted of digestion with 1 mg/ml thermolysin at 37° C. for 3 hours. Mass spectrometry was used to determine the presence of the LKPNM peptide. The results are shown in Table 1. The LKPNM peptide was found to be in samples from positive clones 2, 7, and 11, but not from negative clone 6 and the pET negative control.

The LKPMN peptide was found to represent as much as 3.5% (35 mg/g) of the total soluble protein present.

TABLE 1

| SAMPLES | HEAT 10 MIN. (mg/g total soluble protein) | HEAT 10 MIN DIGEST 1 HOUR (mg/g total soluble protein) |
|---|---|---|
| pET | 0 | 0.25 |
| Clone 2 | 0.035 | 35.7 |
| Clone 6 | 0 | 0.06 |
| Clone 7 | 0 | 18.2 |
| Clone 11 | 0 | 34.7 |

Example 6

Production of Alternative Repeating Unit Peptides

As will be apparent to one of ordinary skill in the art, the present invention is not limited to the specific peptide disclosed in Examples 1–5. For example and without limitation, the present invention can be used to produce proteins containing tandem repeats of the sequences VVYP and VPP. VVYP repeating proteins can be produced by synthesis of pools of polynucleotides and their complements with the following forward and reverse sequences:

5'GTNGTNTAYCCNGTNGTNTAYCCNGT-NGTNTAYCCNGTNGTNTAYCCN3' (SEQ ID NO: 11)

5'NGGRTANACNACNGGRTANACNACNGGR-TANACNACNGGRTANACNAC3' (SEQ ID NO: 12).

After self assembly of the repeating unit polynucleotides by the present method as demonstrated in Example 1, restriction enzymes sites such as BamHI and HindIII, respectively, can be added using the following forward and reverse primers:

5'AAAGGATCCGTNGTNTAYCCNGTNGTNTAYCCN3' (SEQ ID NO: 13)

5'CCCAAGCTTNGGRTANACNACNGGRTANACNAC3' (SEQ ID NO: 14)

To produce proteins containing tandem repeats of the VPP peptides, polynucleotides are synthesized from the following forward and reverse sequences:

5'GTNCCNCCNGTNCCNCCNGTNCCNC-CNGTNCCNCCNGTNCCNCCN3' (SEQ ID NO: 15)

5 'NGGNGGNACNGGNGGNACNGGNGGNAC-NGGNGGNACNGGNGGNAC3' (SEQ ID NO: 16)

and BamHI and HindIII restriction sites can be added after self assembly using the forward and reverse primers:

5'AAAGGATCCGTNCCNCCNGTNCCNC-CNGTNCCNCCN3' (SEQ ID NO: 17)

5'AATAAGCTTNGGNGGNACNGGNGGNAC-NGGNGGNAC3' (SEQ ID NO: 18)

Based on these examples, it will be clear to one of ordinary skill in the art that additional proteins containing tandem repeats of peptides can be designed for use in the present invention without undue experimentation based on known amino acid sequences and standard molecular biology techniques.

Example 7

Tandem Repeats of Multiple Peptides

Although in the preceding examples, only a single peptide was repeated, the present method is not so limited. Within the scope of the present invention, therefore, is the production of polynucleotides comprising tandem repeats of sequences encoding more than one peptide. The sequences encoding the peptides can include additional nucleotides encoding amino acids allowing for the cleavage of the resulting repeating protein between the peptides by, for example, digestive enzymes. Alternatively, the polynucleotides can be designed so that there are no additional nucleotides present between the sequences encoding the peptides of interest. For example, a pool of degenerate polynucleotides encoding repeats of the sequence VPPLKPNM (SEQ ID NO: 19) and their complements can be synthesized. The sequences for the forward and reverse strands, respectively, are:

5'GTNCCNCCNCTNAARCCNAAYATGGTNC-
  CNCCNCTNAARCCNAAYATG3' (SEQ ID NO: 20)

5'CATRTTNGGYTTNAGNGGNGGNACC-
  ATRTTNGGYTTNAGNGGNGGNAC3' (SEQ ID NO: 21)

These polynucleotides can be self assembled into polynucleotides of varying lengths encoding repeats of the VPPLKPNM sequence using the method of the present invention as in Example 1. If desired, restriction sites for EcoRI and NotI can be added after self assembly as described in Example 2 by the use of the following forward and reverse primers, respectively:

5'GCATGAATTCGTNCCNCCNCTNAARC-
  CNAAYATGGTNCCNCCNCTNAARCCN AAYATG3' (SEQ ID NO: 22)

5'GCATGCGGCCGCCATRTTNGGYTT-
  NAGNCGNGGNCCRAANGGNGGNAGCAT RTTNG-
  GYTTNAGNCGNGGNCCRAANGGNGGNAC3' (SEQ ID NO: 23)

In another embodiment, polynucleotides encoding repeats of the peptides LKPNM and VPP separated by the amino acid sequence FGPR (SEQ ID NO: 24) which serves as a cleavage site for digestive enzymes can be designed. Pools of polynucleotides can be synthesized using the following forward and reverse sequences:

5'GTNCCNCCNTTYGGNCCNCGNCTNAARC-
  CNAAYATGGTNCCNCCNTTYGGN CCNCGNCT-
  NAARCGNAAYATG3' (SEQ ID NO: 25)

5'CATRTTNGGYTTNAGNCGNGGNC-
  CRAANGGNGGNAGCATRTTNGGYTTNAG
  NCGNGGNCCRAANGGNGGNAC3' (SEQ ID NO: 26)

Using the present method, these polynucleotides can be rapidly assembled into repeating units of degenerate polynucleotides encoding the peptides of interest, which can then be inserted into appropriate expression vectors and used to transform suitable host cells. For insertion into expression vectors after self-assembly, EcoRI and NotI restriction sites can be added using the following forward and reverse primers:

5'GCATGAATTCGTNCCNCCNTTYGGNC-
  CNCGNCTNAARCCNAAYATGGTNCCN CCNTTYG-
  GNCCNCGNCTNAARCGNAAYATG3' (SEQ ID NO: 27)

5'GCATGCGGCCGCCATRTTNGGYTT-
  NAGNCGNGGNCCRAANGGNGGNAGCAT RTTNG-
  GYTTNAGNCGNGGNCCRAANGGNGGNAC3' (SEQ ID NO: 28)

For example, and without limitation, expression vectors containing the degenerate repeating sequences can be used to transform plant cells so that the resulting plants produce proteins containing multiple repeats of the VPPFGPRLKPNM (SEQ ID NO: 29) sequence. Upon ingestion of material obtained from such a plant, for example, the plant itself or seeds or fruit from the plant, the action of the digestive enzymes trypsin and chymotrypsin would cleave the repeating protein to produce LKPNM and VPP monomers. In this example, trypsin which cleaves on the C-terminal side of arginine, will cleave after the R in the FGPR sequence and chymotrypsin which cleaves on the C-terminal side of hydrophobic residues will cleave after the P in VPP and after the M in LKPNM. In the case where the FGPR sequence is absent, only chymotrypsin is needed to produce the VPP and LKPMN peptides. It will be clear to those of ordinary skill in the art that alternative enzymatic cleavage sites in addition to the sites given in this example could be utilized.

CONCLUSION

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method for producing a recombinant protein containing repeating units comprising:
   (a) providing a first pool of polynucleotides comprising codons, said pool of polynucleotides comprising at least two tandem repeats of sequences encoding a portion of said recombinant protein, wherein said tandem repeats contain degenerate nucleotide sequences encoding for a portion of said recombinant protein in accordance with the degeneracy of the genetic code;
   (b) providing a second pool of polynucleotides, at least some of which are complementary to the polynucleotides in said first pool of polynucleotides;
   (c) combining said first pool of polynucleotides and said second pool of polynucleotides under conditions whereby the polynucleotides will anneal;
   (d) extending the 3' ends of said annealed polynucleotides under conditions wherein said annealed polynucleotides act as primers for their complements;
   (e) denaturing the extended polynucleotides;
   (f) repeating steps (c)–(e) at least once, whereby the products of step (e) provide the polynucleotides for annealing in step (c) of the next cycle;
   (g) if necessary, adding one or more linker oligonucleotides to the end of the products of (f), said linker oligonucleotides containing at least one restriction enzyme cleavage site;
   (h) inserting the products of (f) or (g) into a suitable vector;
   (i) introducing said vector into a suitable host cell; and
   (j) maintaining said host cell under conditions allowing for expression of said recombinant protein.

2. The method of claim 1, wherein said tandem repeats are separated by no more than nine nucleotides.

3. The method of claim 1, further comprising cleaving said recombinant protein between said repeating units to produce non-repeating peptides.

4. The method of claim 3, further comprising cleaving said polynucleotides after step (f).

5. The method of claim 1, wherein at least 25% of the codons in said polynucleotides encode a desired amino acid.

6. The method of claim 1, wherein at least 50% of the codons in said polynucleotides encode a desired amino acid.

7. The method of claim 1, wherein at least 75% of the codons in said polynucleotides encode a desired amino acid.

8. The method of claim 1, wherein at least 90% of the codons in said palynucleotides encode a desired amino acid.

9. The method of claim 1, wherein said tandem repeats encode at least one sequence selected from the group consisting of LKPNM (SEQ ID NO:1), KPNM (SEQ ID NO:2), VVYP (SEQ ID NO:3), KPN, DKP, YKP, EKP, DAP, EAP, HPP, VPP, LK, PN and NM.

10. The method of claim 1, further comprising introducing a second vector into said host cell, said second vector containing a nucleotide sequence encoding an enzyme capable of cleaving said recombinant protein between said repeating units.

11. The method of claim 10, wherein said second vector further comprises a tissue or organelle specific promoter such that expression of said enzyme is restricted to a tissue or organelle different from the tissue or organelle expressing said recombinant protein.

12. The method of claim 10, wherein said second vector further comprises a plastid targeting sequence.

13. The method of claim 1, wherein said vector further comprises an expression cassette.

14. The method of claim 13, wherein said expression cassette comprises at least one promoter chosen from the group consisting of a tissue specific promoter, an inducible promoter, a constitutive promoter, a developmentally regulated promoter, an organelle specific promoter, a seed specific promoter and a plastid specific promoter.

15. The method of claim 13, wherein said expression cassette further comprises at least one plastid targeting sequence.

16. The method of claim 13, wherein said expression cassette further comprises at least one secretion sequence.

17. The method of claim 13, wherein said expression cassette further comprises an additional nucleotide sequence encoding an enzyme capable of cleaving said recombinant protein between said repeating units.

18. The method of claim 17, wherein said additional nucleotide sequence is under the control of a separate promoter.

19. The method of claim 1, wherein said host cell is selected from the group consisting of bacterial cells, yeast cells, insect cells and animal cells.

20. The method of claim 1, wherein said host cell is a plant cell.

* * * * *

UNITED STATES PATENT AND TRADEMARK OFFICE
CERTIFICATE OF CORRECTION

| | | |
|---|---|---|
| PATENT NO. | : 7,060,467 B2 | |
| APPLICATION NO. | : 09/804733 | |
| DATED | : June 13, 2006 | |
| INVENTOR(S) | : Wang et al. | |

It is certified that error appears in the above-identified patent and that said Letters Patent is hereby corrected as shown below:

In claim 8, column 41, line 61, delete "palynucleotides" and insert --polynucleotides-- therefor.

Signed and Sealed this

Twenty-second Day of August, 2006

JON W. DUDAS
*Director of the United States Patent and Trademark Office*

SEQUENCE LISTING

```
<160> NUMBER OF SEQ ID NOS: 29

<210> SEQ ID NO 1
<211> LENGTH: 5
<212> TYPE: PRT
<213> ORGANISM: Euthynnus pelamis
<220> FEATURE:
<221> NAME/KEY: PEPTIDE
<222> LOCATION: (1)..(5)

<400> SEQUENCE: 1

Leu Lys Pro Asn Met
1               5

<210> SEQ ID NO 2
<211> LENGTH: 4
<212> TYPE: PRT
<213> ORGANISM: Euthynnus pelamis
<220> FEATURE:
<221> NAME/KEY: PEPTIDE
<222> LOCATION: (1)..(4)

<400> SEQUENCE: 2

Lys Pro Asn Met
1

<210> SEQ ID NO 3
<211> LENGTH: 4
<212> TYPE: PRT
<213> ORGANISM: Euthynnus pelamis
<220> FEATURE:
<221> NAME/KEY: PEPTIDE
<222> LOCATION: (1)..(4)

<400> SEQUENCE: 3

Val Val Tyr Pro
1

<210> SEQ ID NO 4
<211> LENGTH: 15
<212> TYPE: DNA
<213> ORGANISM: Artificial Sequence
<220> FEATURE:
<221> NAME/KEY: misc_feature
<222> LOCATION: (1)..(15)
<223> OTHER INFORMATION: Degenerate sequence
<221> NAME/KEY: misc_feature
<222> LOCATION: (1)..(15)
<223> OTHER INFORMATION: n=a, t, c or g; r=a or g; y=c or t

<400> SEQUENCE: 4
ctnaarccna ayatg                                              15

<210> SEQ ID NO 5
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: n=any nucleotide; r=a or g; y=c or t
<221> NAME/KEY: misc_feature
<222> LOCATION: (1)..(60)
<223> OTHER INFORMATION: Degenerate sequence

<400> SEQUENCE: 5
ctnaarccna ayatgctnaa rccnaayatg ctnaarccna ayatgctnaa rccnaayatg    60
```

<210> SEQ ID NO 6
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: n=any nucleotide, r=a or g, y=c or t
<221> NAME/KEY: misc_feature
<222> LOCATION: (1)..(60)
<223> OTHER INFORMATION: degenerate sequence

<400> SEQUENCE: 6
catrttnggy ttnagcatrt tnggyttnag catrttnggy ttnagcatrt tnggyttnag          60

<210> SEQ ID NO 7
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Primer
<221> NAME/KEY: misc_feature
<222> LOCATION: (1)..(25)
<223> OTHER INFORMATION: n=any nucleotide; r=a or g; y=c or t

<400> SEQUENCE: 7
aaagaattcc tnaarccnaa yatgc          25

<210> SEQ ID NO 8
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: Primer
<221> NAME/KEY: misc_feature
<222> LOCATION: (1)..(27)
<223> OTHER INFORMATION: n=any nucleotide; r=a or g; y=c or t

<400> SEQUENCE: 8
aaagcggccg ccatrttngg yttnagc          27

<210> SEQ ID NO 9
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Primer

<400> SEQUENCE: 9
taatacgact cactataggg          20

<210> SEQ ID NO 10
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Primer

<400> SEQUENCE: 10
cgatcaataa cgagtcgcc          19

<210> SEQ ID NO 11
<211> LENGTH: 48
<212> TYPE: DNA
<213> ORGANISM: Artificial Sequence
<220> FEATURE:
<221> NAME/KEY: misc_feature
<222> LOCATION: (1)..(48)
<223> OTHER INFORMATION: n=any nucleotide; y=c or t
<221> NAME/KEY: misc_feature
<222> LOCATION: (1)..(48)
<223> OTHER INFORMATION: Degenerate sequence

<400> SEQUENCE: 11
gtngtntayc cngtngtnta yccngtngtn tayccngtng tntayccn           48

<210> SEQ ID NO 12
<211> LENGTH: 48
<212> TYPE: DNA
<213> ORGANISM: Artificial Sequence
<220> FEATURE:
<221> NAME/KEY: misc_feature
<222> LOCATION: (1)..(48)
<223> OTHER INFORMATION: n=any nucleotide; r=a or g
<221> NAME/KEY: misc_feature
<222> LOCATION: (1)..(48)
<223> OTHER INFORMATION: Degenerate sequence

<400> SEQUENCE: 12
nggrtanacn acnggrtana cnacnggrta nacnacnggr tanacnac            48

<210> SEQ ID NO 13
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: Forward primer
<221> NAME/KEY: misc_feature
<222> LOCATION: (1)..(33)
<223> OTHER INFORMATION: n=any nucleotide; y=c or t

<400> SEQUENCE: 13
aaaggatccg tngtntaycc ngtngtntay ccn                            33

<210> SEQ ID NO 14
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: Reverse primer
<221> NAME/KEY: misc_feature
<222> LOCATION: (1)..(33)
<223> OTHER INFORMATION: n=any nucleotide; r=a or g

<400> SEQUENCE: 14
cccaagcttn ggrtanacna cnggrtanac nac                            33

<210> SEQ ID NO 15
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: n=any nucleotide
<221> NAME/KEY: misc_feature

```
<222> LOCATION: (1)..(45)
<223> OTHER INFORMATION: Degenerate sequence

<400> SEQUENCE: 15
gtnccnccng tnccnccngt nccnccngtn ccnccngtnc cnccn                   45

<210> SEQ ID NO 16
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: n=any nucleotide
<221> NAME/KEY: misc_feature
<222> LOCATION: (1)..(45)
<223> OTHER INFORMATION: Degenerate sequence

<400> SEQUENCE: 16
nggnggnacn ggnggnacng gnggnacngg nggnacnggn ggnac                   45

<210> SEQ ID NO 17
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Forward primer
<221> NAME/KEY: misc_feature
<222> LOCATION: (1)..(36)
<223> OTHER INFORMATION: n=any nucleotide

<400> SEQUENCE: 17
aaaggatccg tnccnccngt nccnccngtn ccnccn                             36

<210> SEQ ID NO 18
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Reverse primer
<221> NAME/KEY: misc_feature
<222> LOCATION: (1)..(36)
<223> OTHER INFORMATION: n=any nucleotide

<400> SEQUENCE: 18
aataagcttn ggnggnacng gnggnacngg nggnac                             36

<210> SEQ ID NO 19
<211> LENGTH: 8
<212> TYPE: PRT
<213> ORGANISM: Artificial Sequence
<220> FEATURE:
<221> NAME/KEY: VARIANT
<222> LOCATION: (1)..(8)
<223> OTHER INFORMATION: Fusion protein

<400> SEQUENCE: 19

Val Pro Pro Leu Lys Pro Asn Met
1               5

<210> SEQ ID NO 20
<211> LENGTH: 48
<212> TYPE: DNA
<213> ORGANISM: Artificial Sequence
<220> FEATURE:
```

```
<221> NAME/KEY: misc_feature
<222> LOCATION: (1)..(48)
<223> OTHER INFORMATION: n=any nucleotide; r=a or g; y=c or t
<221> NAME/KEY: misc_feature
<222> LOCATION: (1)..(48)
<223> OTHER INFORMATION: Degenerate sequence

<400> SEQUENCE: 20
gtnccnccnc tnaarccnaa yatggtnccn ccnctnaarc cnaayatg                48

<210> SEQ ID NO 21
<211> LENGTH: 48
<212> TYPE: DNA
<213> ORGANISM: Artificial Sequence
<220> FEATURE:
<221> NAME/KEY: misc_feature
<222> LOCATION: (1)..(48)
<223> OTHER INFORMATION: n=any nucleotide; r=a or g; y=c or t
<221> NAME/KEY: misc_feature
<222> LOCATION: (1)..(48)
<223> OTHER INFORMATION: Degenerate sequence

<400> SEQUENCE: 21
catrttnggy ttnagnggng gnaccatrtt nggyttnagn ggnggnac                48

<210> SEQ ID NO 22
<211> LENGTH: 58
<212> TYPE: DNA
<213> ORGANISM: Artificial Sequence
<220> FEATURE:
<221> NAME/KEY: misc_feature
<222> LOCATION: (1)..(58)
<223> OTHER INFORMATION: Forward primer
<221> NAME/KEY: misc_feature
<222> LOCATION: (1)..(58)
<223> OTHER INFORMATION: n=any nucleotide; r=a or g; y=c or t

<400> SEQUENCE: 22
gcatgaattc gtnccnccnc tnaarccnaa yatggtnccn ccnctnaarc cnaayatg      58

<210> SEQ ID NO 23
<211> LENGTH: 84
<212> TYPE: DNA
<213> ORGANISM: Artificial Sequence
<220> FEATURE:
<221> NAME/KEY: misc_feature
<222> LOCATION: (1)..(84)
<223> OTHER INFORMATION: Reverse primer
<221> NAME/KEY: misc_feature
<222> LOCATION: (1)..(84)
<223> OTHER INFORMATION: n=any nucleotide; r=a or g; y=c or t

<400> SEQUENCE: 23
gcatgcggcc gccatrtttng gyttnagncg nggnccraan ggnggnagca trtttnggytt  60 nagncgnggn ccraanggng gnac                                          84

<210> SEQ ID NO 24
<211> LENGTH: 4
<212> TYPE: PRT
<213> ORGANISM: Artificial Sequence
<220> FEATURE:
<221> NAME/KEY: VARIANT
<222> LOCATION: (1)..(4)
<223> OTHER INFORMATION: Trypsin cleavage site

<400> SEQUENCE: 24

Phe Gly Pro Arg
 1
```

<210> SEQ ID NO 25
<211> LENGTH: 72
<212> TYPE: DNA
<213> ORGANISM: Artificial Sequence
<220> FEATURE:
<221> NAME/KEY: misc_feature
<222> LOCATION: (1)..(72)
<223> OTHER INFORMATION: Forward primer
<221> NAME/KEY: misc_feature
<222> LOCATION: (1)..(72)
<223> OTHER INFORMATION: n=any nucleotide; r=a or g; y=c or t

<400> SEQUENCE: 25
gtnccnccnt tyggnccncg nctnaarccn aayatggtnc cnccnttygg nccncgnctn    60
aarcgnaaya tg    72

<210> SEQ ID NO 26
<211> LENGTH: 72
<212> TYPE: DNA
<213> ORGANISM: Artificial Sequence
<220> FEATURE:
<221> NAME/KEY: misc_feature
<222> LOCATION: (1)..(72)
<223> OTHER INFORMATION: Reverse primer
<221> NAME/KEY: misc_feature
<222> LOCATION: (1)..(72)
<223> OTHER INFORMATION: n=any nucleotide; r=a or g; y=c or t

<400> SEQUENCE: 26
catrttnggy ttnagncgng gnccraangg nggnagcatr ttnggyttna gncgnggncc    60
raanggnggn ac    72

<210> SEQ ID NO 27
<211> LENGTH: 82
<212> TYPE: DNA
<213> ORGANISM: Artificial Sequence
<220> FEATURE:
<221> NAME/KEY: misc_feature
<222> LOCATION: (1)..(82)
<223> OTHER INFORMATION: Forward primer
<221> NAME/KEY: misc_feature
<222> LOCATION: (1)..(82)
<223> OTHER INFORMATION: n=any nucleotide; r=a or g; y=c or t

<400> SEQUENCE: 27
gcatgaattc gtnccnccnt tyggnccncg nctnaarccn aayatggtnc cnccnttygg    60
nccncgnctn aarcgnaaya tg    82

<210> SEQ ID NO 28
<211> LENGTH: 84
<212> TYPE: DNA
<213> ORGANISM: Artificial Sequence
<220> FEATURE:
<221> NAME/KEY: misc_feature
<222> LOCATION: (1)..(84)
<223> OTHER INFORMATION: Reverse primer
<221> NAME/KEY: misc_feature
<222> LOCATION: (1)..(84)
<223> OTHER INFORMATION: n=any nucleotide; r=a or g; y=c or t

<400> SEQUENCE: 28
gcatgcggcc gccatrttng gyttnagncg nggnccraan ggnggnagca trttnggytt    60
nagncgnggn ccraanggng gnac    84

<210> SEQ ID NO 29
<211> LENGTH: 12

```
-continued

<212> TYPE: PRT
<213> ORGANISM: Artificial Sequence
<220> FEATURE:
<221> NAME/KEY: VARIANT
<222> LOCATION: (1)..(12)
<223> OTHER INFORMATION: Fusion protein

<400> SEQUENCE: 29

Val Pro Pro Phe Gly Pro Arg Leu Lys Pro Asn Met
1               5                   10
```